United States Patent [19]

Fields et al.

[11] Patent Number: 4,732,970

[45] Date of Patent: Mar. 22, 1988

[54] ANTITUMOR AMINO ACID AND PEPTIDE DERIVATIVES OF 1,4-BIS(AMINOALKYL AND HYDROXY-AMINOALKYL)AMINO)-5,8-DIHYDROXYANTHRAQUINONES

[75] Inventors: Thomas L. Fields; Keith C. Murdock, both of Pearl River; Martin L. Sassiver, Spring Valley; Janis Upeslacis, Pomona, all of N.Y.

[73] Assignee: American Cyanamid Company, Stamford, Conn.

[21] Appl. No.: 874,195

[22] Filed: Jun. 13, 1986

[51] Int. Cl.[4] .......................... C07K 5/00; C07K 5/02; C07K 7/00; C07C 103/75
[52] U.S. Cl. .................................. 530/323; 530/332; 530/338; 530/331; 530/330; 530/329; 530/328; 530/327; 530/326; 260/377
[58] Field of Search ............... 530/326, 327, 328, 329, 530/330, 331, 338, 332, 323; 514/19, 18, 17, 16, 15; 564/157; 260/377

[56] References Cited

U.S. PATENT DOCUMENTS 4,298,523 11/1981 Heavner .............................. 530/338
4,526,989 7/1985 Murdock et al. ................... 549/316

OTHER PUBLICATIONS

Anderson et al., J. Am. Chem. Soc., vol. 86, pp. 1839–1842 (1964).

*Primary Examiner*—Delbert R. Phillips
*Assistant Examiner*—Christina Chan
*Attorney, Agent, or Firm*—Edward A. Conroy, Jr.

[57] ABSTRACT

Antitumor amino acid and peptide derivatives of 1,4-bis[(aminoalkyl and hydroxyaminoalkyl)amino]-5,8-dihydroxyanthraquinones.

20 Claims, No Drawings

ANTITUMOR AMINO ACID AND PEPTIDE DERIVATIVES OF 1,4-BIS(AMINOALKYL AND HYDROXY-AMINOALKYL)AMINO)-5,8-DIHYDROXYANTHRAQUINONES

BRIEF SUMMARY OF THE INVENTION

This invention relates to new organic compounds which are represented by the formula:

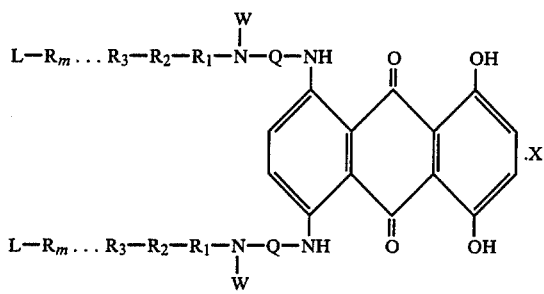

wherein Q is a divalent moiety selected from the group consisting of

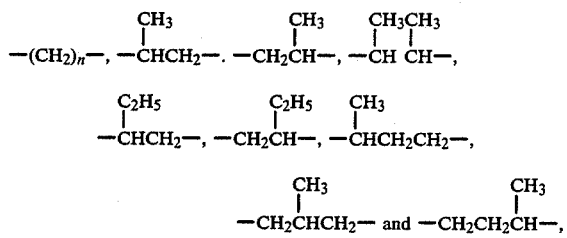

where n is an integer from 2 to 4 inclusive; W is selected from the group consisting of hydrogen and 2-hydroxyethyl; L is selected from the group consisting of hydrogen, carbobenzyloxy, tertiary-butyloxycarbonyl, and fluoroenylmethoxycarbonyl; $R_1$, $R_2$, $R_3$ ... $R_m$ are independently selected from the group of D or L amino acids consisting of cysteine, leucine, isoleucine, phenylalanine, tyrosine, proline, tryptophan, hydroxyproline, aspartic acid, asparagine, glutamic acid, glutamine, lysine, ornithine, arginine, histidine, alanine, glycine, methionine, valine, threonine and serine which are linked through amide bonds between the $\alpha$-amino functionality of one amino acid and the carboxyl group of the adjacent amino acid, and in those amino acids which possess side-chain functionality, the side-chains can be optionally substituted by protecting groups, as for example, aspartic acid and glutamic acid can be incorporated containing lower alkyl, benzyl or 4-nitrobenzyl esters as part of the side chain carboxyl group, or lysine and ornithine can contain carbobenzyloxy, tertiary-butyloxy, fluorenylmethoxycarbonyl protecting groups on the side-chain amino functionality, or arginine can be incorporated containing carbobenzyloxycarbonyl, tertiary-butyloxycarbonyl or nitro protection of the guanidinium functionality, or cysteine can be incorporated with tertiary-butyl or acetyl groups on the side-chain sulfhydryl group; m is an integer 1 to 10 inclusive; and X is a pharmacologically acceptable organic or inorganic acid-addition salt or combination of salts.

DETAILED DESCRIPTION OF THE INVENTION

The compounds of this invention may be prepared according to the following reaction sequence.

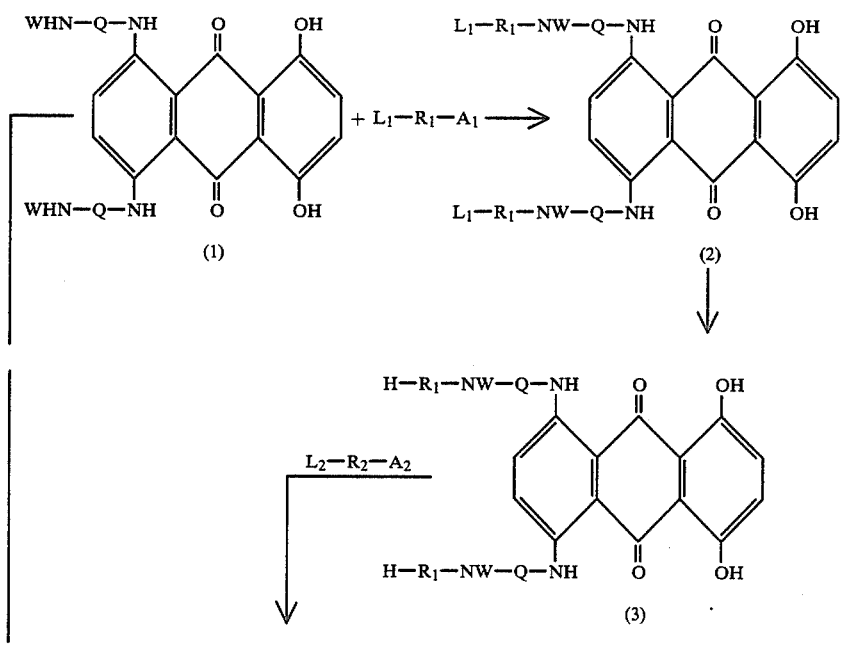

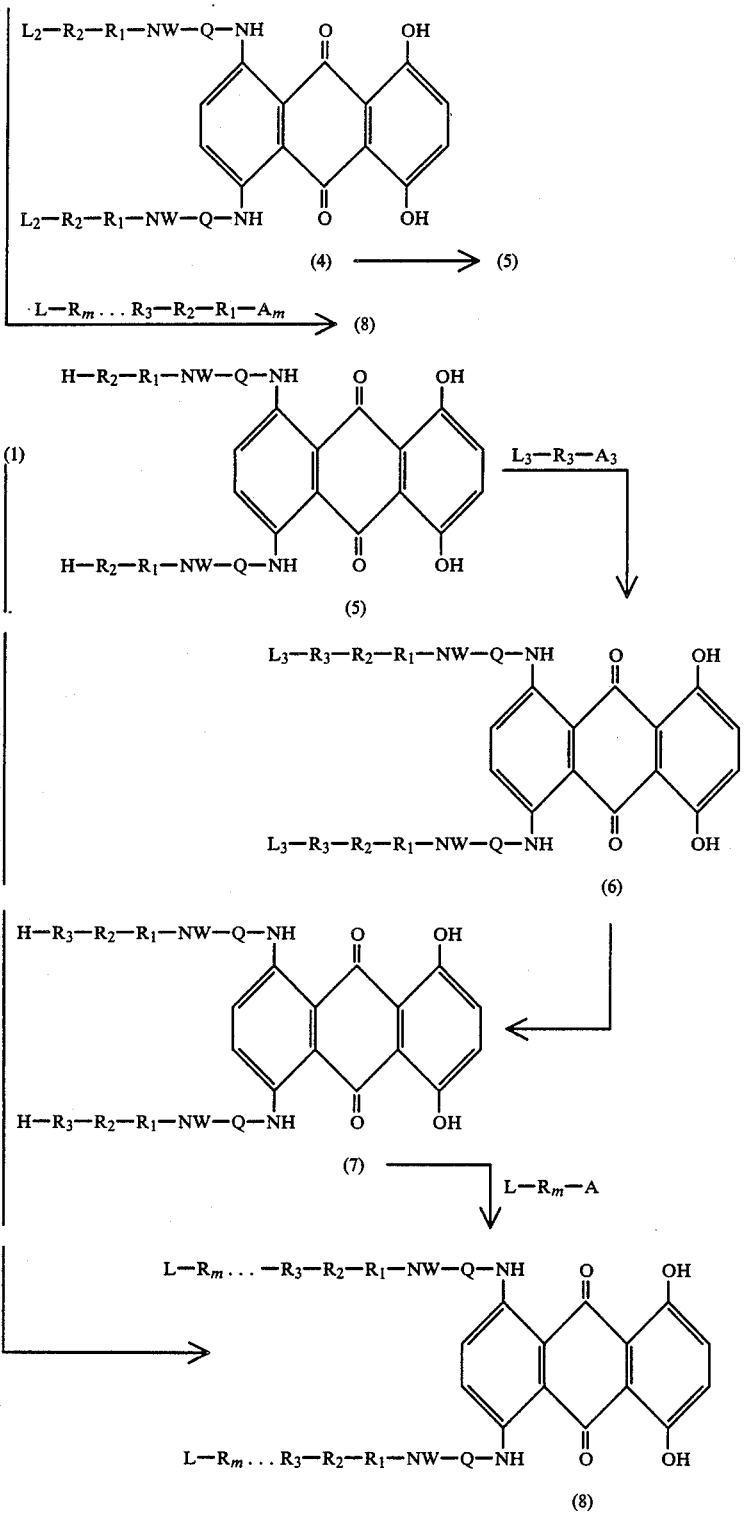

In accordance with the above reaction scheme, the anthraquinone (1), where Q and W are as described above is dissolved in a solvent such as dimethylformamide containing an organic base such as triethylamine or diisopropylethylamine, or alternatively, in dry tetrahydrofuran in the presence of trimethylsilyl chloride and triethylamine. The solution is chilled, and to this is added the first amino acid ($R_1$), activated through its carboxyl group as its corresponding hydroxysuccinimide ester, or as the isobutyryl chloroformate, or as a mixed or symmetrical anhydride, or as any one of a number of carboxyl activating functionalities known to those skilled in the art of peptide synthesis. The α-amino group of the activated acid must be protected at this point by a group such as tertiary-butyloxycarbonyl, benzyloxycarbonyl, fluorenylmethoxycarbonyl, and the like, to avoid interference during condensation with the anthraquinones of this invention. Similarly, those amino acids which contain functionality in their side-chains in general also need to have the functionality protected, and are selected as described previously. The protecting groups used on the side chain can be the same or different than those used to protect the α-amino radical. The activated, protected amino acid ($L_1$-$R_1$-$A_1$) is dissolved in the same solvent used to dissolve the anthraquinone, and addition is done dropwise with stirring. The reaction is stirred at 0° to 40° C., preferably at room temperature, for about 24 hours, then filtered and the desired amide (2) is isolated either by precipitation with a solvent of low polarity, or by evaporation. The protecting group ($L_1$) on the α-amine is then removed such that elongation of the peptide chain can be achieved if desired. For example, the tertiarybutyloxycarbonyl group can be removed by dissolving (2) in anisole, cooling the solution in an ice bath and adding trifluoroacetic acid. The solution is stirred briefly in the cold, then warmed to room temperature for 1–24 hours. The desired deprotected product (3) is isolated by diluting the reaction with a solvent in which the product is not soluble, for example, diethyl ether, and the precipitate collected by filtration. Alternatively, the tertiarybutyloxycarbonyl group can be removed by dissolving the compound (2) in a mixture of acetic acid and anisole, then hydrogen chloride gas is bubbled into the solution for a few minutes. After standing at room temperature for 1–24 hours, the absence of (2) is determined by a technique such as thin layer chromatography or analytical high pressure liquid chromatography, then the product (3) is isolated by precipitation as described above. A benzyloxycarbonyl group can be removed by dissolving (2) in a solvent such as acetic acid, cooling, but not freezing the solution, and bubbling in gaseous hydrobromic acid. After the reaction has remained at room temperature for 1–24 hours and absence of starting material has been determined, the product (3) is isolated by precipitation. Alternatively, the benzyloxycarbonyl group can be removed by hydrogenation of (2) in the presence of a noble metal catalyst such as palladium on carbon, but in this case re-oxidation of the reduced anthraquinone ring is generally necessary. A fluorenylmethoxycarbonyl group can be removed by dissolving (2) in a polar solvent such as dimethylformamide and adding a secondary amine such as dimethylamine. The product (3) is again isolated either by precipitation or by evaporation of the reaction solution.

If desired, the next amino acid fragment ($R_2$) is then added by repeating the sequence of reacting (3) with an α-amino and side-chain protected, carboxy group activated amino acid derivative, isolating the intermediate (4) and removing the α-amino protecting group as described above. The process is repeated by judicious manipulation of the above conditions, or by applying conditions familiar to those skilled in the art of peptide synthesis until the entire desired peptide sequence (8) has been assembled.

Alternatively, the entire peptide sequence can be assembled prior to formation of the amide bond between the peptide carboxy terminus and the anthraquinone nucleus. This can be accomplished by applying the solution techniques described above or assembling the peptide chain using any one of the techniques which have been developed as modifications of the Merrifield solid phase peptide synthesis procedure.

Removal of side-chain protecting groups, where desirable, and where these groups are the tertiarybutyloxycarbonyl, benzyloxycarbonyl or fluorenylmethoxycarbonyl radicals is accomplished as described above. In addition, the tertiary-butyloxy group required for protection of aspartic and glutamic acids is removed under the acid hydrolysis conditions described for cleavage of the tertiary-butyloxycarbonyl protecting group. Most other groups are removed by slight modifications of the above-described procedures.

The starting materials (1) where W is hydrogen are described in U.S. patent application, Ser. No. 87,354, filed Oct. 23, 1979 now U.S. Pat. No. 4,526,989.

The starting materials (1) where W is —$CH_2CH_2OH$ are described in U.S. Pat. No. 4,197,249.

The novel compounds of the present invention possess the property of inhibiting the growth of leukemia and solid tumors in mammals as established by the following tests.

Lymphocytic Leukemia P388 Test

The animals used were $BDF_1$ mice, all of one sex, weighing a minimum of 18 g and all within a 3 g weight range. There were 5 or 6 mice per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 (relative to tumor inocu-lation) at various doses. The animals were weighed and survivors recorded on a regular basis for 60 days. The median survival time and the ratio of survival time for treated (T)/control (C) animals were calculated. The positive control compound was 5-fluorouracil. The results of this test appear in Table I.

TABLE I

| Lymphocytic Leukemia P388 | | | |
|---|---|---|---|
| Compound | Dose (mg/kg) | Median Survival (Days) | T/C × 100 (%) |
| [S—(R*,R*)]—N,N'—[(9,10-di-hydro-5,8-dihydroxy-9,10-dioxo-1,4-anthracenediyl)bis(imino-2,1-ethanediyl)]bis[2-amino-4-methylpentanamide]dihydro-chloride | 3 1.5 0.75 | 18.0 26.0 25.5 | 150 217 213 |
| Control | — | 12.0 | — |
| Positive control | 60 | 23.0 | 192 |
| [R—(R*,R*)]—N,N'—[(9,10-di-hydro-5,8-dihydroxy-9,10-dioxo-1,4-anthracenediyl)bis(imino-2,1-ethanediyl)]bis[2-aminopropanamide]dihydrochloride | 3 1.5 0.75 | 24.0 20.0 19.0 | 218 182 173 |
| Control | — | 11.0 | — |
| Positive control | 60 | 21.5 | 195 |
| [S—(R*,R*)]—N,N'—[(9,10-di-hydro-5,8-dihydroxy-9,10-dioxo-1,4-anthracenediyl)bis(imino-2,1-ethanediyl)]bis[2-aminopropanamide]dihdrochloride | 3 1.5 0.75 | 42.5 52.5 25.5 | 386 477 232 |
| Control | — | 11.0 | — |
| Positive control | 60 | 21.5 | 195 |
| [S—(R*,R*)]—N,N'—[(9,10-di-hydro-5,8-dihydroxy-9,10-dioxo-1,4-anthracenediyl)bis(imino-2,1-ethanediyl)]bis[2-amino-benzenepropanamide]dihydro-chloride | 3 1.5 0.75 | 19.5 23.0 22.5 | 163 192 188 |
| Control | — | 12.0 | — |
| Positive control | 60 | 23.0 | 192 |
| N,N'—[(9,10-dihydro-5,8-dihydroxy-9,10-dioxo-1,4-anthracenediyl)bis(imino-2,1-ethanediyl)]bis[2-aminoacetamide]-dihydrochloride | 3 1.5 0.75 | 34.5 24.0 22.0 | 288 200 183 |

TABLE I-continued

Lymphocytic Leukemia P388

| Compound | Dose (mg/kg) | Median Survival (Days) | T/C × 100 (%) |
|---|---|---|---|
| Control | — | 12.0 | — |
| Positive control | 60 | 23.0 | 192 |
| [R—(R*,R*)]—N,N'—[(9,10-dihydro-5,8-dihydroxy-1,4-anthracenediyl)bis(imino-2,1-ethanediyl)]bis[2-amino-4-methylpentanamide]dihydrochloride | 3 | 23.5 | 196 |
|  | 1.5 | 22.5 | 188 |
|  | 0.75 | 20.5 | 171 |
| Control | — | 12.0 | — |
| Positive control | 60 | 23.0 | 192 |
| [S—(R*,R*)]—N,N'—[(9,10-dihydro-5,8-dihydroxy-9,10-dioxo-1,4-anthracenediyl)bis(imino-2,1-ethanediyl)]bis[2-amino-N—(2-hydroxyethyl)-4-methylpentanamide]dihydrochloride | 3 | 17.0 | 155 |
|  | 1.5 | 14.0 | 127 |
|  | 0.75 | 12.0 | 109 |
| Control | — | 11.0 | — |
| Positive control | 60 | 22.5 | 205 |
| [R—(R*,R*)]—N,N'—[(9,10-dihydro-5,8-dihydroxy-9,10-dioxo-1,4-anthracenediyl)bis(imino-2,1-ethanediyl)]bis[2-amino-N—(2-hydroxyethyl)-4-methylpentanamide]tris(trifluoroacetate) | 3 | 15.5 | 141 |
|  | 1.5 | 13.0 | 118 |
|  | 0.75 | 12.0 | 109 |
| Control | — | 11.0 | — |
| Positive control | 60 | 22.5 | 205 |
| [S—(R*,R*)]—N,N'—[(9,10-dihydro-5,8-dihydroxy-9,10-dioxo-1,4-anthracenediyl)bis(imino-2,1-ethanediyl)]bis[2-amino-4-(methylthio)butanamide]dihydrochloride | 3 | 25.5 | 255 |
|  | 1.5 | 20.5 | 205 |
|  | 0.75 | 17.0 | 170 |
| Control | — | 10.0 | — |
| Positive control | 60 | 25.0 | 250 |
| [S—(R*,R*)]—N,N'—[(9,10-dihydro-5,8-dihydroxy-9,10-dioxo-1,4-anthracenediyl)bis(imino-2,1-ethanediyl)]bis[2-amino-4-methylpentanamide]dihydrobromide | 3 | 21.0 | 210 |
|  | 1.5 | 18.0 | 180 |
|  | 0.75 | 17.5 | 175 |
| Control | — | 10.0 | — |
| Positive control | 60 | 25.0 | 250 |
| [S—(R*,R*)]—N,N'—[(9,10-dihydro-5,8-dihydroxy-9,10-dioxo-1,4-anthracenediyl)bis(imino-2,1-ethanediyl)]bis[2,6-diaminohexanamide]tetrahydrobromide | 3 | 13.0 | 130 |
|  | 1.5 | 33.0 | 330 |
|  | 0.75 | 23.0 | 230 |
| Control | — | 10.0 | — |
| Positive control | 60 | 25.0 | 250 |
| [S—(R*,R*,R*,R*)]—N,N'—[(9,10-dihydro-5,8-dihydroxy-9,10-dioxo-1,4-anthracenediyl)bis(imino-2,1-ethanediyl)]bis[2-amino-3-methylpentanamide]dihydrochloride | 3 | 22.5 | 225 |
|  | 1.5 | 18.0 | 180 |
|  | 0.75 | 18.5 | 185 |
| Control | — | 10.0 | — |
| Positive control | 60 | 25.0 | 250 |
| N,N'—[(9,10-dihydro-5,8-dihydroxy-9,10-dioxo-1,4-anthracenediyl)bis(imino-2,1-ethanediyl)]bis[L-leucyl-L-alaninamide]dihydrobromide | 3 | 20.0 | 200 |
|  | 1.5 | 20.0 | 200 |
|  | 0.75 | 17.0 | 170 |
| Control | — | 10.0 | — |
| Positive control | 60 | 25.0 | 250 |
| N,N'—[(9,10-dihydro-5,8-dihydroxy-9,10-dioxo-1,4-anthracenediyl)bis(imino-2,1-ethanediyl)]bis[L-leucyl-L-alanyl-L-leucinamide]dihydrobromide | 3 | 25.0 | 250 |
|  | 1.5 | 25.5 | 255 |
|  | 0.75 | 20.5 | 205 |
| Control | — | 10.0 | — |
| Positive control | 60 | 25.0 | 250 |
| N,N'—[(9,10-dihydro-5,8-dihydroxy-9,10-dioxo-1,4-anthracenediyl)bis(imino-2,1-ethanediyl)]bis[N—[(phenylmethoxy)carbonyl]-L-leucyl-L-alanyl-L-leucinamide] | 3 | 17.0 | 155 |
|  | 1.5 | 19.0 | 173 |
|  | 0.75 | 20.0 | 182 |
| Control | — | 11.0 | — |
| Positive control | 60 | 18.0 | 164 |
| N,N'—[(9,10-dihydro-5,8-dihydroxy-9,10-dioxo-1,4-anthracenediyl)bis(imino-2,1-ethanediyl)]bis[N—[(phenylmethoxy)carbonyl]-L-glycly-L-phenylalaninamide] | 3 | 19.0 | 173 |
|  | 1.5 | 17.5 | 159 |
|  | 0.75 | 18.5 | 168 |
| Control | — | 11.0 | — |
| Positive control | 60 | 20.5 | 186 |
| [S—(R*,R*)]-5,5'-[(9,10-dihydro-5,8-dihydroxy-9,10-dioxo-1,4-anthracenediyl)bis(imino-2,1-ethanediylimino)]bis[4-amino-5-oxopentanoic acid]dihydrochloride | 3 | 41.0 | 410 |
|  | 1.5 | 24.5 | 245 |
|  | 0.75 | 22.0 | 220 |
| Control | — | 10.0 | — |
| Positive control | 60 | 18.0 | 180 |
| [S—(R*,R*)]—N,N'—[(9,10-dihydro-5,8-dihydroxy-9,10-dioxo-1,4-anthracenediyl)bis(imino-2,1-ethanediyl)]bis[2-amino-3-methylbutanamide]dihydrochloride | 3 | 20.0 | 200 |
|  | 1.5 | 20.0 | 200 |
|  | 0.75 | 18.5 | 185 |
| Control | — | 10.0 | — |
| Positive control | 60 | 18.0 | 180 |
| [S—(R*,R*)]—N,N'—[(9,10-dihydro-5,8-dihydroxy-9,10-dioxo-1,4-anthracenediyl)bis(imino-2,1-ethanediyl)]bis[glycyl-L-phenylalaninamide]dihydrobromide | 3 | 19.0 | 190 |
|  | 1.5 | 19.0 | 195 |
|  | 0.75 | 18.5 | 185 |
| Control | — | 10.0 | — |
| Positive control | 60 | 18.0 | 180 |
| [2S—(2R*,2'R*,3S*,3'S*)]—N,N'—[(9,10-dihydro-5,8-dihydroxy-9,10-dioxo-1,4-anthracenediyl)bis(imino-2,1-ethanediyl)]bis[2-amino-3-hydroxybutanamide]bis(trifluoroacetate) | 3 | 33.5 | 335 |
|  | 1.5 | 22.5 | 225 |
|  | 0.75 | 21.0 | 210 |
| Control | — | 10.0 | — |
| Positive control | 60 | 18.0 | 180 |
| N,N'—[(9,10-dihydro-5,8-dihydroxy-9,10-dioxo-1,4-anthracenediyl)bis(imino-2,1-ethanediyl)]bis[glycyl-L-prolyl-L-leucylglycyl-L-prolinamide]dihydrobromide | 3 | 24.5 | 245 |
|  | 1.5 | 22.0 | 220 |
|  | 0.75 | 19.0 | 190 |
| Control | — | 10.0 | — |
| Positive control | 60 | 18.0 | 180 |
| N,N'—[(9,10-dihydro-5,8-dihydroxy-9,10-dioxo-1,4-anthracenediyl)bis(imino-2,1-ethanediyl)]bis[glycyl-L-prolylglycyl-L-alaninamide]dihydrobromide | 3 | 25.5 | 255 |
|  | 1.5 | 20.5 | 205 |
|  | 0.75 | 19.5 | 195 |
| Control | — | 10.0 | — |
| Positive control | 60 | 18.0 | 180 |
| [R—(R*,R*)]—N,N'—[(9,10-dihydro-5,8-diyroxy-9,10-dioxo-1,4-anthracenediyl)bis(imino-2,1-ethanediyl)]bis[2-amino-3-mercaptopropanamide]dihydrobromide | 3 | 24.5 | 245 |
|  | 1.5 | 23.0 | 230 |
|  | 0.75 | 21.0 | 210 |
| Control | — | 10.0 | — |
| Positive control | 60 | 18.0 | 180 |
| N,N'—[(9,10-dihydro-5,8-dihydroxy-9,10-dioxo-1,4-anthracenediyl)bis(imino-2,1-ethanediyl)]bis[N—[(phenylmethoxy)carbonyl]glycylglycinamide] | 3 | 15.0 | 136 |
|  | 1.5 | 14.0 | 127 |
|  | 0.75 | 12.0 | 109 |
| Control | — | 11.0 | — |
| Positive control | 60 | 18.0 | 164 |
| N,N'—[(9,10-dihydro-5,8-dihydroxy-9,10-dioxo-1,4-anthracenediyl)bis(imino-2,1-ethanediyl)]bis[glycylglycinamide]- | 3 | 24.0 | 218 |
|  | 1.5 | 21.5 | 195 |
|  | 0.75 | 22.0 | 200 |

TABLE I-continued
Lymphocytic Leukemia P388

| Compound | Dose (mg/kg) | Median Survival (Days) | T/C × 100 (%) |
|---|---|---|---|
| hydrobromide | | | |
| Control | — | 11.0 | — |
| Positive control | 60 | 21.0 | 191 |
| N,N'—[(9,10-dihydro-5,8-dihydroxy-9,10-dioxo-1,4-anthracenediyl)bis(imino-2,1-ethanediyl)]bis[N—[(1,1-dimethylethoxy)carbonyl]glycylglycylglycinamide] | 3 | 18.0 | 164 |
| | 1.5 | 15.5 | 141 |
| | 0.75 | 15.0 | 136 |
| Control | — | 11.0 | — |
| Positive control | 60 | 18.0 | 164 |
| N,N'—[(9,10-dihydro-5,8-dihydroxy-9,10-dioxo-1,4-anthracenediyl)bis(imino-2,1-ethanediyl)]bis[glycylglycylglycinamide]bis(trifluoroacetate) | 3 | 22.0 | 200 |
| | 1.5 | 23.0 | 209 |
| | 0.75 | 19.5 | 177 |
| Control | — | 11.0 | — |
| Positive control | 60 | 21.0 | 191 |
| N,N'—[(9,10-dihydro-5,8-dihydroxy-9,10-dioxo-1,4-anthracenediyl)bis(imino-2,1-ethanediyl)]bis[N—[(phenylmethoxy)carbonyl]-L-alanylglycinamide] | 3 | 19.0 | 173 |
| | 1.5 | 13.0 | 118 |
| | 0.75 | 12.5 | 114 |
| Control | — | 11.0 | — |
| Positive control | 60 | 20.5 | 186 |
| [S—(R*,R*)]—N,N'—[(9,10-dihydro-5,8-dihydroxy-9,10-dioxo-1,4-anthracenediyl)bis(imino-2,1-ethanediyl)]bis[2-amino-3-(4-hydroxyphenyl)propanamide]dihydrochloride | 3 | 23.5 | 214 |
| | 1.5 | 23.5 | 214 |
| | 0.75 | 25.0 | 227 |
| Control | — | 11.0 | — |
| Positive control | 60 | 20.5 | 186 |
| N,N'—[(9,10-dihydro-5,8-dihydroxy-9,10-dioxo-1,4-anthracenediyl)bis(imino-2,1-ethanediyl)]bis[L-alanylglycinamine]dihydrobromide | 3 | 32.5 | 295 |
| | 1.5 | 28.0 | 255 |
| | 0.75 | 21.0 | 191 |
| Control | — | 11.0 | — |
| Positive control | 60 | 20.5 | 186 |
| N,N'—[(9,10-dihydro-5,8-dihydroxy-9,10-dioxo-1,4-anthracenediyl)bis(imino-2,1-ethanediyl)]bis[N—[(1,1-dimethylethoxy)carbonyl]-L-alanyl-L-leucinamide] | 3 | 13.5 | 123 |
| | 1.5 | 12.0 | 109 |
| | 0.75 | 12.0 | 109 |
| Control | — | 11.0 | — |
| Positive control | 60 | 18.0 | 164 |
| N,N'—[(9,10-dihydro-5,8-dihydroxy-9,10-dioxo-1,4-anthracenediyl)bis(imino-2,1-ethanediyl)]bis[L-alanyl-L-leucinamide]bis(trifluoroacetate) | 3 | 28.0 | 255 |
| | 1.5 | 20.0 | 182 |
| | 0.75 | 19.0 | 173 |
| Control | — | 11.0 | — |
| Positive control | 60 | 18.0 | 164 |
| N,N'—[(9,10-dihydro-5,8-dihydroxy-9,10-dioxo-1,4-anthracenediyl)bis(imino-2,1-ethanediyl)]bis[N—[(1,1-dimethylethoxy)carbonyl]-L-alanyl-L-alanyl-L-leucinamide] | 3 | 16.0 | 160 |
| | 1.5 | 16.5 | 165 |
| | 0.75 | 15.5 | 155 |
| Control | — | 10.0 | — |
| Positive control | 60 | 22.0 | 220 |
| N,N'—[(9,10-dihydro-5,8-dihydroxy-9,10-dioxo-1,4-anthracenediyl)bis(imino-2,1-ethanediyl)]bis[N—[(phenylmethoxy)carbonyl]glycylglycyl-L-leucinamide | 3 | 18.0 | 180 |
| | 1.5 | 17.0 | 170 |
| | 0.75 | 17.0 | 170 |
| Control | — | 10.0 | — |
| Positive control | 60 | 22.0 | 220 |
| N,N'—[(9,10-dihydro-5,8-dihydroxy-9,10-dioxo-1,4-anthracenediyl)bis(imino-2,1-ethanediyl)]bis[L-alanyl-L-alanyl-L-leucinamide]bis(trifluoroacetate) | 3 | 22.0 | 220 |
| | 1.5 | 21.5 | 215 |
| | 0.75 | 21.0 | 210 |
| Control | — | 10.0 | — |
| Positive control | 60 | 22.0 | 220 |
| N,N'—[(9,10-dihydro-5,8-dihydroxy-9,10-dioxo-1,4-anthracenediyl)bis(imino-2,1-ethanediyl)]bis[glycylglycyl-L-leucinamide]dihydrobromide | 3 | 44.5 | 445 |
| | 1.5 | 22.5 | 225 |
| | 0.75 | 22.0 | 220 |
| Control | — | 10.0 | — |
| Positive control | 60 | 22.0 | 220 |
| N,N'—[(9,10-dihydro-5,8-dihydroxy-9,10-dioxo-1,4-anthracenediyl)bis(imino-2,1-ethanediyl)]bis[L-alanyl-L-alanine]bis(trifluoroacetate) | 3 | 23.0 | 219 |
| | 1.5 | 20.0 | 190 |
| | 0.75 | 20.0 | 190 |
| Control | — | 10.5 | — |
| Positive control | 60 | 20.5 | 195 |
| N,N'—[(9,10-dihydro-5,8-dihydroxy-9,10-dioxo-1,4-anthracenediyl)bis(imino-2,1-ethanediyl)]bis[N—[(1,1-dimethylethoxy)carbonyl]-L-alanyl-L-alanyl-L-alanine] | 3 | 19.0 | 181 |
| | 1.5 | 18.0 | 171 |
| | 0.75 | 18.5 | 176 |
| Control | — | 10.5 | — |
| Positive control | 60 | 20.5 | 195 |
| N,N'—(9,10-dihydro-5,8-dihydroxy-9,10-dioxo-1,4-anthracenediyl)bis(imino-2,1-ethanediyl)]bis[L-alanyl-L-alanyl-L-alanine]bis(trifluoroacetate) | 3 | 40.0 | 381 |
| | 1.5 | 24.5 | 233 |
| | 0.75 | 21.0 | 200 |
| Control | — | 10.5 | — |
| Positive control | 60 | 20.5 | 195 |
| [S—(R*,R*)][(9,10-dihydro-5,8-dihdroxy-9,10-dioxo-1,4-anthracenediyl)bis[imino-2,1-ethanediylimino[2-oxo-1-[(phenylmethoxy)methyl]-2,1-ethanediyl]]]bis carbamic acid, bis-(1,1-dimethylethyl)ester | 3 | 15.5 | 155 |
| | 1.5 | 13.5 | 135 |
| | 0.75 | 12.0 | 120 |
| Control | — | 10.0 | — |
| Positive control | 60 | 20.0 | 200 |
| [S—(R*,R*)]—N,N'—[(9,10-dihydro-5,8-dihydroxy-9,10-dioxo 1,4-anthracenediyl)bis(imino-2,1-ethanediyl)]bis[2-amino-3-(phenylmethoxy)propanamide]bis(trifluoroacetate) | 3 | 19.5 | 195 |
| | 1.5 | 21.5 | 215 |
| | 0.75 | 19.5 | 195 |
| Control | — | 10.0 | — |
| Positive control | 60 | 20.0 | 200 |
| [S—(R*,R*)][(9,10-dihydro-5,8-dihydroxy-9,10-dioxo-1,4-anthracenediyl)bis[imino-2,1-ethanediylimino[1-hydroxymethyl]-2-oxo-2,1-ethanediyl]]]carbamic acid, bis(1,1-dimethylethyl)ester | 3 | 17.5 | 159 |
| | 1.5 | 16.0 | 145 |
| | 0.75 | 13.5 | 123 |
| Control | — | 11.0 | — |
| Positive control | 60 | 21.0 | 191 |
| [S—(R*,R*)]—N,N'—[(9,10-dihydro-5,8-dihyroxy-9,10-dioxo-1,4-anthracenediyl)bis(imino-2,1-ethanediyl)]bis[2-amino-3-hydroxypropanamide]bis(trifluoroacetate) | 3 | 23.5 | 214 |
| | 1.5 | 19.0 | 173 |
| | 0.75 | 19.0 | 173 |
| Control | — | 11.0 | — |
| Positive control | 60 | 21.0 | 191 |
| [S—(R*,R*)]—5,5'-[(9,10-dihydro-5,8-dihydroxy-9,10-dioxo-1,4-anthracenediyl)bis(imino-2,1-ethanediyl)]bis[4-[[(1,1-dimethylethoxy)carbonyl]amino]-5-oxopentanoic acid]bis(phenylmethyl)ester | 3 | 18.0 | 164 |
| | 1.5 | 17.0 | 155 |
| | 0.75 | 16.5 | 150 |
| Control | — | 11.0 | — |
| Positive control | 60 | 20.0 | 182 |
| [S—(R*,R*)]—4,4'-[(9,10-dihydro-5,8-dihydroxy-9,10-dioxo-1,4-anthracenediyl)bis(imino- | 3 | 18.0 | 164 |
| | 1.5 | 15.5 | 141 |
| | 0.75 | 14.0 | 127 |

TABLE I-continued

Lymphocytic Leukemia P388

| Compound | Dose (mg/kg) | Median Survival (Days) | T/C × 100 (%) |
|---|---|---|---|
| 2,1-ethanediylimino)]bis[3-[[(1,1-dimethylethoxy)carbonyl]amino]-4-oxobutanoic acid]bis(phenylmethyl)ester | | | |
| Control | — | 11.0 | — |
| Positive control | 60 | 20.0 | 182 |
| [S—(R*,R*)]—5,5'-[(9,10-dihydro-5,8-dihydroxy-9,10-dioxo-1,4-anthracenediyl)bis(imino-2,1-ethanediylimino)]bis[5-oxo-4-[[(phenylmethoxy)carbonyl]amino]pentanoic acid]bis(1,1-dimethylethyl)ester | 3 | 16.5 | 150 |
| | 1.5 | 17.0 | 155 |
| | 0.75 | 15.0 | 136 |
| Control | — | 11.0 | — |
| Positive control | 60 | 20.0 | 182 |
| [S—(R*,R*)]—5,5'-[(9,10-dihydro-5,8-dihydroxy-9,10-dioxo-1,4-anthracenediyl)bis(imino-2,1-ethanediylimino)]bis[4-amino-5-oxopentanoic acid]bis(phenylmethyl)ester, bis(trifluoroacetate) | 3 | 24.0 | 218 |
| | 1.5 | 19.5 | 177 |
| | 0.75 | 18.0 | 164 |
| Control | — | 11.0 | — |
| Positive control | 60 | 20.0 | 182 |
| [S—(R*,R*)]—4,4'-[(9,10-dihydro-5,8-dihydroxy-9,10-dioxo-1,4-anthracenediyl)bis(imino-2,1-ethanediylimino)]bis[3-amino-4-oxobutanoic acid]bis(phenylmethyl)ester, bis(trifluoroacetate) | 3 | 26.0 | 236 |
| | 1.5 | 25.5 | 232 |
| | 0.75 | 21.0 | 191 |
| Control | — | 11.0 | — |
| Positive control | 60 | 20.0 | 182 |
| [S—(R*,R*)]—4,4'-[(9,10-dihydro-5,8-dihydroxy-9,10-dioxo-1,4-anthracenediyl)bis(imino-2,1-ethanediylimino)]bis[3-[[(9H—fluoren-9-ylmethoxy)carbonyl]amino]-4-oxobutanoic acid]bis(1,1-dimethylethyl)ester | 3 | 16.0 | 133 |
| | 1.5 | 15.0 | 125 |
| | 0.75 | 13.0 | 108 |
| Control | — | 12.0 | — |
| Positive control | 60 | 22.5 | 188 |
| [S—(R*,R*)]—4,4'-[(9,10-dihydro-5,8-dihydroxy-9,10-dioxo-1,4-anthracenediyl)bis(imino-2,1-ethanediylimino)]bis[3-amino-4-oxobutanoic acid]bis(1,1-dimethylethyl)ester | 3 | 19.0 | 158 |
| | 1.5 | 19.5 | 163 |
| | 0.75 | 21.5 | 179 |
| Control | — | 12.0 | — |
| Positive control | 60 | 22.5 | 188 |
| [S—(R*,R*)]—4,4'-[(9,10-dihydro-5,8-dihydroxy-9,10-dioxo-1,4-anthracenediyl)bis(imino-2,1-ethanediylimino)]bis[3-amino-4-oxobutanoic acid]bis(trifluoroacetate) | 3 | 23.0 | 192 |
| | 1.5 | 19.5 | 163 |
| | 0.75 | 23.0 | 192 |
| Control | — | 12.0 | — |
| Positive control | 60 | 22.5 | 188 |
| N,N'—[(9,10-dihydro-5,8-dihydroxy-9,10-dioxo-1,4-anthracenediyl)bis[imino-2,1-ethanediyl)]bis[N—[(1,1-dimethylethoxy)carbonyl]-L-seryl-L-alaninamide] | 3 | 21.0 | 175 |
| | 1.5 | 19.0 | 158 |
| | 0.75 | 18.5 | 154 |
| Control | — | 12.0 | — |
| Positive control | 60 | 14.0 | 117 |
| N,N'—[(9,10-dihydro-5,8-dihydroxy-9,10-dioxo-1,4-anthracenediyl)bis(imino-2,1-ethanediyl)]bis[L-seryl-L-alaninamide]bis(trifluoroacetate) | 3 | 22.5 | 188 |
| | 1.5 | 22.5 | 188 |
| | 0.75 | 22.0 | 183 |
| Control | — | 12.0 | — |
| Positive control | 60 | 14.0 | 117 |
| N,N'—[(9,10-dihydro-5,8-dihydroxy-9,10-dioxo-1,4-anthracenediyl)bis(imino-2,1-ethanediyl)]bis[N—[(9H—fluoren-9-ylmethoxy)carbonyl]-L-α-aspartyl-L-seryl-L-alaninamide]bis(1,1-dimethylethyl)ester | 3 | 22.5 | 188 |
| | 1.5 | 20.0 | 167 |
| | 0.75 | 20.0 | 167 |
| Control | — | 12.0 | — |
| Positive control | 60 | 14.0 | 117 |
| [S—(R*,R*)]—5,5'-[(9,10-dihydro-5,8-dihydroxy-9,10-dioxo-1,4-anthracenediyl)bis(imino-2,1-ethanediylimino)]bis[5-oxo-4-[[(phenylmethoxy)carbonyl]amino]pentanoic acid] | 3 | 16.5 | 138 |
| | 1.5 | 15.0 | 125 |
| | 0.75 | 14.0 | 117 |
| Control | — | 12.0 | — |
| Positive control | 60 | 22.5 | 188 |
| N,N'—[(9,10-dihydro-5,8-dihydroxy-9,10-dioxo-1,4-anthracenediyl)bis(imino-2,1-ethanediyl)]bis[L-α-aspartyl-L-seryl-L-alaninamide]bis(1,1-dimethylethyl)ester | 3 | 22.5 | 188 |
| | 1.5 | 23.0 | 192 |
| | 0.75 | 18.0 | 150 |
| Control | — | 12.0 | — |
| Positive control | 60 | 14.0 | 117 |
| N,N'—[(9,10-dihydro-5,8-dihydroxy-9,10-dioxo-1,4-anthracenediyl)bis(imino-2,1-ethanediyl)]bis[N—[(9H—fluoren-9-ylmethoxy)carbony[]-L-α-aspartyl-L-alanyl-L-alaninamide]bis(1,1-dimethylethyl)ester | 3 | 19.0 | 173 |
| | 1.5 | 18.0 | 164 |
| | 0.75 | 18.5 | 168 |
| Control | — | 11.0 | — |
| Positive control | 60 | 23.0 | 209 |
| N,N'—[(9,10-dihydro-5,8-dihydroxy-9,10-dioxo-1,4-anthracenediyl)bis(imino-2,1-ethanediyl)]bis[L-α-aspartyl-L-alanyl-L-alaninamide]bis(1,1-dimethylethyl)ester | 3 | 26.0 | 236 |
| | 1.5 | 19.5 | 177 |
| | 0.75 | 19.0 | 173 |
| Control | — | 11.0 | — |
| Positive control | 60 | 23.0 | 209 |
| N,N'—[(9,10-dihydro-5,8-dihydroxy-9,10-dioxo-1,4-anthracenediyl)bis(imino-2,1-ethanediyl)]bis[N—[(9H—fluoren-9-ylmethoxy)carbony[]-L-α-aspartyl-L-alanyl-L-leucinamide]bis(1,1-dimethylethyl)ester | 3 | 19.0 | 173 |
| | 1.5 | 18.5 | 168 |
| | 0.75 | 16.0 | 145 |
| Control | — | 11.0 | — |
| Positive control | 60 | 23.0 | 209 |
| N,N'—[(9,10-dihydro-5,8-dihydroxy-9,10-dioxo-1,4-anthracenediyl)bis(imino-2,1-ethanediyl)]bis[L-α-aspartyl-L-alanyl-L-leucinamide]bis(1,1-dimethylethyl)ester | 3 | 19.0 | 173 |
| | 1.5 | 19.0 | 173 |
| | 0.75 | 21.0 | 191 |
| Control | — | 11.0 | — |
| Positive control | 60 | 22.0 | 200 |
| N,N'—[(9,10-dihydro-5,8-dihydroxy-9,10-dioxo-1,4-anthracenediyl)bis(imino-2,1-ethanediyl)]bis[L-α-aspartyl-L-alanyl-L-alaninamide]bis(trifluoroacetate) | 3 | 38.5 | 385 |
| | 1.5 | 22.5 | 225 |
| | 0.75 | 22.0 | 220 |
| Control | — | 10.0 | — |
| Positive control | 60 | 21.0 | 210 |
| N,N'—[(9,10-dihydro-5,8-dihydroxy-9,10-dioxo-1,4-anthracenediyl)bis(imino-2,1-ethanediyl)]bis[L-α-aspartyl-L-alanyl-L-leucinamide]bis(trifluoroacetate) | 3 | 28.0 | 280 |
| | 1.5 | 21.5 | 215 |
| | 0.75 | 24.0 | 240 |
| Control | — | 10.0 | — |
| Positive control | 60 | 21.0 | 210 |
| [S—(R*,R*)][(9,10-dihydro-5,8-dihydroxy-9,10-dioxo-1,4-anthracenediyl)bis[1-[3-[[imino(nitroamino)methyl]amino]propyl]-2-oxo-2,1-ethane- | 3 | 18.0 | 164 |
| | 1.5 | 16.5 | 150 |
| | 0.75 | 15.5 | 141 |

TABLE I-continued

Lymphocytic Leukemia P388

| Compound | Dose (mg/kg) | Median Survival (Days) | T/C × 100 (%) |
|---|---|---|---|
| diyl]]bis carbamic acid, bis-(phenylmethyl)ester | | | |
| Control | — | 11.0 | — |
| Positive control | 60 | 21.0 | 191 |
| N,N'—[(9,10-dihydro-5,8-dihydroxy-9,10-dioxo-1,4-anthracenediyl)bis[2-amino-5-[[imino-(nitroamino)methyl]amino]pentanamide]tetrahydrobromide | 3 | 25.5 | 232 |
| | 1.5 | 21.5 | 195 |
| | 0.75 | 18.5 | 168 |
| Control | — | 11.0 | — |
| Positive control | 60 | 21.0 | 191 |
| [S—(R*,R*)][(9,10-dihydro-5,8-dihydroxy-9,10-dioxo-1,4-anthracenediyl)bis[imino-2,1-ethanediylimino[1-[3-[[imino-[(phenylmethoxy)carbonyl]-amino]methyl][(phenylmethoxy)-carbonyl]amino]propyl]-2-oxo-2,1-ethanediyl]]]carbamic acid, bis(phenylmethyl)ester | 3 | 16.0 | 145 |
| | 1.5 | 16.0 | 145 |
| | 0.75 | 14.0 | 127 |
| Control | — | 11.0 | — |
| Positive control | 60 | 21.0 | 191 |
| N,N'—[(9,10-dihydro-5,8-dihydroxy-9,10-dioxo-1,4-anthracenediyl)bis(imino-2,1-ethanediyl)]bis[L-arginyl-L-seryl-L-alaninamide]tetrahydrobromide | 3 | 34.5 | 314 |
| | 1.5 | 21.0 | 191 |
| | 0.75 | 21.5 | 195 |
| Control | — | 11.0 | — |
| Positive control | 60 | 21.0 | 191 |
| N,N'—[(9,10-dihydro-5,8-dihydroxy-9,10-dioxo-1,4-anthracenediyl)bis(imino-2,1-ethanediyl)]bis[N—[(1,1-dimethylethoxy)carbonyl]-L-alanyl-L-argininamide]tetrahydrobromide | 3 | 20.5 | 205 |
| | 1.5 | 19.0 | 190 |
| | 0.75 | 17.0 | 170 |
| Control | — | 10.0 | — |
| Positive control | 60 | 22.0 | 220 |
| N,N'—[(9,10-dihydro-5,8-dihydroxy-9,10-dioxo-1,4-anthracenediyl)bis(imino-2,1-ethanediyl)]bis[L-alanyl-L-argininamide]tetrahydrobromide | 3 | 44.0 | 440 |
| | 1.5 | 33.0 | 330 |
| | 0.75 | 22.5 | 225 |
| Control | — | 10.0 | — |
| Positive control | 60 | 22.0 | 220 |
| N,N'—[(9,10-dihydro-5,8-dihydroxy-9,10-dioxo-1,4-anthracenediyl)bis(imino-2,1-ethanediyl)]bis[N—[(1,1-dimethylethoxy)carbonyl]-L-alanyl-L-alanyl-L-argininamide]dihydrobromide | 3 | 24.5 | 223 |
| | 1.5 | 17.5 | 159 |
| | 0.75 | 17.0 | 155 |
| Control | — | 11.0 | — |
| Positive control | 60 | 17.0 | 155 |
| N,N'—[(9,10-dihydro-5,8-dihydroxy-9,10-dioxo-1,4-anthracenediyl)bis(imino-2,1-ethanediyl)]bis[L-alanyl-L-argininamide]bis(trifluoroacetate) | 3 | 19.5 | 177 |
| | 1.5 | 23.5 | 214 |
| | 0.75 | 23.5 | 214 |
| Control | — | 11.0 | — |
| Positive control | 60 | 17.0 | 155 |
| [S—(R*,R*)][(9,10-dihydro-5,8-dihydroxy-9,10-dioxo-1,4-anthracenediyl)bis(imino-2,1-ethanediylimino[1-[3-[(aminoiminomethyl)amino]propyl]-2-oxo-2,1-ethanediyl]]]carbamic acid, bis(phenylmethyl)ester, dihydrobromide | 3 | 22.5 | 188 |
| | 1.5 | 21.0 | 175 |
| | 0.75 | 21.5 | 179 |
| Control | — | 12.0 | — |
| Positive control | 60 | 14.0 | 117 |
| [S—(R*,R*)]—N,N'—[(9,10-dihydro-5,8-dihydroxy-9,10-dioxo-1,4-anthracenediyl)bis(imino-2,1-ethanediyl)]bis[2-amino-5-[(aminoiminomethyl)amino]pentanamide]hexahydrobromide | 3 | 34.5 | 314 |
| | 1.5 | 27.0 | 245 |
| | 0.75 | 22.0 | 200 |
| Control | — | 11.0 | — |
| Positive control | 60 | 22.0 | 200 |
| N,N'—[(9,10-dihydro-5,8-dihydroxy-9,10-dioxo-1,4-anthracenediyl)bis(imino-2,1-ethanediyl)]bis[N²—[(phenylmethoxy)carbonyl]-L-arginyl-L-seryl-L-alaninamide]dihydrobromide | 3 | 24.5 | 223 |
| | 1.5 | 22.5 | 205 |
| | 0.75 | 22.5 | 200 |
| Control | — | 11.0 | — |
| Positive control | 60 | 21.0 | 191 |

Melanotic Melanoma B16

The animals used were BDF1 mice, all of the same sex, weighing a minimum of 17 g and all within a 3 g weight range. There were 12 animals per test group. A 1 g portion of melanotic melanoma B16 tumor was homogenized in 10 ml of cold balanced salt solution and a 0.5 ml aliquot of the homogenate was implanted intraperitoneally into each of the test mice. The test compounds were administered intraperitoneally on days 1, 5 and 9 (relative to tumor inoculation) at various doses. The animals were weighed and survivors recorded on a regular basis for 60 days. The median survival time and ratio of survival time for treated (T)/control (C) animals were calculated. The positive control compound was 1,4-bis[(2-aminoethyl)amino]-5,8-dihydroxyanthraquinone, dihydrochloride (U.S. patent application Ser. No. 87,354, filed Oct. 23, 1979). The results of this test on representative compounds of this invention appear in Table II.

TABLE II

Melanotic Melanoma B16

| Compound | Dose (mg/kg) | Median Survival (Days) | T/C × 100 (%) |
|---|---|---|---|
| N,N'—[(9,10-dihydro-5,8-dihydroxy-9,10-dioxo-1,4-anthracenediyl)bis(imino-2,1-ethanediyl)]bis[2-aminoacetamide]-dihydrochloride | 3 | 37.0 | 218 |
| | 1.5 | 28.0 | 165 |
| | 0.75 | 27.5 | 162 |
| Control | — | 17.0 | — |
| Positive control | 1.5 | 46.5 | 274 |
| [S—(R*,R*)]—N,N'—[(9,10-dihydro-5,8-dihroxy-9,10-dioxo-1,4-anthracenediyl)bis(imino-2,1-ethanediyl)]bis[2,6-diaminohexanamide]tetrahydrobromide | 3 | 25.5 | 162 |
| | 1.5 | 37.5 | 221 |
| | 0.75 | 26.5 | 156 |
| Control | — | 17.0 | — |
| Positive control | 1.5 | 46.5 | 274 |
| [S—(R*,R*)]—5,5'-[(9,10-dihydro-5,8-dihydroxy-9,10-dioxo-1,4-anthracenediyl)bis(imino-2,1-ethanediyl)]bis[4-amino-5-oxopentanoic acid]dihydrochloride | 3 | 22.0 | 129 |
| | 1.5 | 31.0 | 182 |
| | 0.75 | 27.5 | 162 |
| Control | — | 17.0 | — |
| Positive control | 1.5 | 46.5 | 274 |
| [2S—(2R*,2'R*,3S*,3'S*)]—N,N'—[(9,10-dihydro-5,8-dihydroxy-9,10-dioxo-1,4-anthracenediyl)-bis(imino-2,1-ethanediyl)]bis-2-amino-3-hydroxybutanamide]-bis(trifluoroacetate) | 3 | 40.0 | 235 |
| | 1.5 | 39.5 | 232 |
| | 0.75 | 35.0 | 206 |
| Control | — | 17.0 | — |
| Positive control | 1.5 | 46.5 | 274 |

The active compounds of the present invention inhibit the growth of tumors in mammals and induce regression and/or palliation of leukemia and related cancers in mammals when administered in amounts ranging from about 1 mg to about 1.2 g per square meter of body surface area per day. The interrelationship of dosages for animals of various sizes and species and humans (based on mg/m$^2$ of body surface area) is described by Freireich, E. J., et al., Quantitative Comparison of Toxicity of Anticancer Agents in Mouse, Rat, Hamster, Dog, Monkey and Man. Cancer Chemother. Rep., 50, No. 4, 219–244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. These active compounds may be administered by the intravenous, intramuscular or subcutaneous routes.

The active compounds may be administered parenterally. Solutions or dispersions of the active compound can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable used include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal, and the like. In many cases it will be preferable to include isotonic agents, for example sugars or sodium chloride. Prolonged absorption of the injectable compositions can be brought about by the use in the compositions of agents delaying absorption, for example aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on the unique characteristics of the active material, the particular therapeutic effect to be achieved and the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 mg to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 to 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of a cytotoxic nature to the hosts harboring the cancer. As used herein, cancer disease means blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment.

This invention will be described in greater detail in conjunction with the following non-limiting specific examples.

EXAMPLE 1

[S-(R*,R*)]-N,N'-[(9,10-Dihydro-5,8-dihydroxy-9,10-dioxo-1,4-anthracenediyl)bis[imino-2,1-ethanediylimino-(1-methyl-2-oxo-2,1-ethanediyl)]]bis-carbamic acid, bis(1,1-dimethylethyl)ester A 1.78 g portion of 1,4-bis[(2-aminoethyl)-amino]-5,8-dihydroxyanthraquinone, dihydrochloride (U.S. patent application Ser. No. 87,354, filed Oct. 23, 1979) and 2.53 g of triethylamine were slurried in 50 ml of dry tetrahydrofuran, cooled in an ice-methanol bath. A solution of 2.72 g of trimethyl silyl chloride in 20 ml of dry tetrahydrofuran was added dropwise with stirring. The mixture was stirred in the ice bath for 40 minutes, then at room temperature for 40 minutes and then filtered. The filtrate was cooled in an ice-methanol bath and a solution of 3.15 g of N-tertiary butyloxycarbonyl-L-alanine hydroxy-succinimide ester in 50 ml of dry tetrahydrofuran was added dropwise with stirring. The ice bath was allowed to melt, then the reaction was stirred for 24 hours and finally filtered. The filtrate was passed through a silica gel pad, washed with 500 ml of dry tetrahydrofuran and then concentrated in vacuo at 60° C. The residue was slurried in 50 ml of ethyl acetate, filtered and dried in vacuo giving 584 mg of the desired product, mp 195° C. (dec.).

EXAMPLE 2

[S-(R*,R*)]-N,N'-[(9,10-Dihydro-5,8-dihydroxy-9,10-dioxo-1,4-anthracenediyl)bis[imino-2,1-ethanediyl[(2-hydroxyethyl)imino]-1-(2-methylpropyl)-2-oxo-2,1-ethane-diyl]]]bis-carbamic acid, bis(1,1-dimethylethyl)ester A solution of 618 mg of dicyclohexylcarbodiimide in 5 ml of dry dimethylformamide was added to an ice cooled solution of 1.496 g of N-tertiary butyloxycarbonyl-L-leucine in 15 ml of dry dimethylformamide. This mixture was stirred ½ hour in the cold, then 1.5 hours at room temperature and then filtered. The filtrate, containing tertiary-butyloxycarbonyl-L-leucine anhydride, was added to a solution of 444 mg of 1,4-dihydroxy-5,8-bis[[2-(2-hydroxy-ethylamino)ethyl]amino]anthraquinone (U.S. Pat. No. 4,197,249) and 0.31 ml of triethylamine in 40 ml of dry dimethylformamide, stirred overnight, evaporated to near dryness and diluted with 250 ml of ethyl acetate. This solution was washed repeatedly with water and with saturated aqueous sodium bicarbonate, then evaporated to dryness and dissolved in 50 ml of ether. The ether solution was filtered and the filtrate diluted with 150 ml of hexane. The solid was collected, giving 775 mg of the desired product, mp 105° C. (dec.).

EXAMPLE 3

[S-(R*,R*)]-N,N'-[(9,10-Dihydro-5,8-dihydroxy-9,10-dioxo-1,4-anthracenediyl)bis[imino-2,1-ethanediylimino-2-oxo-1-(phenylmethyl)-2,1-ethanediyl]]]bis-carbamic acid, bis(1,1-dimethylethyl)ester The general procedure of Example 1 was followed using 3.99 g of N-tertiary butyloxycarbonyl L-phenylalanine hydroxysuccinimide ester in place of the L-alanine ester and appropriate amounts of the other reagents, giving 344 mg of the desired product, mp 160° C. (dec.).

EXAMPLE 4

[S-(R*,R*)]-N,N'-[(9,10-Dihydro-5,8-dihydroxy-9,10-dioxo-1,4-anthracenediyl)bis[imino-2,1-ethanediylimino-[1-(2-methylpropyl)-2-oxo-2,1-ethanediyl]]]bis-carbamic acid, bis(1,1-dimethylethyl)ester The general procedure of Example 1 was followed using 3.61 g of N-tertiary butyloxycarbonyl-L-leucine hydroxysuccinimide ester in place of the L-alanine ester and appropriate amounts of the other reagents, giving 713 mg of the desired product, mp 178° C. (dec.).

EXAMPLE 5

N,N'-[(9,10-Dihydro-5,8-dihydroxy-9,10-dioxo-1,4-anthracenediyl)bis[imino-2,1-ethanediylimino-(2-oxo-2,1-ethanediyl)]]bis-carbamic acid, bis(1,1-dimethylethyl)ester The general procedure of Example 1 was followed using 5.99 g of N-tertiary-butyloxycarbonyl-glycine hydroxysuccinimide ester in place of the L-alanine ester and appropriate amounts of the other reagents, giving 4.0 g of the desired product, mp 110° C. (dec.).

EXAMPLE 6

[R-(R*,R*)]-N,N'-[(9,10-Dihydro-5,8-9,10-dioxo-1,4-anthracenediyl)bis[imino-2,1-ethanediylimino-(2-methyllpropyl)-2-oxo-2,1-ethanediyl]]]bis-carbamic acid, bis(1,1-dimethylethyl)ester The general procedure of Example 1 was followed using 1.8 g of N-tertiary-butyloxycarbonyl-D-leucine hydroxysuccinimide ester in place of the L-alanine ester and appropriate amounts of the other reagents, giving 315 mg of the desired product, mp 180° C. (dec.).

EXAMPLE 7

[S-(R*,R*,R*,R*)]-N,N'-[(9,10-Dihydro-5,8--dihydroxy-9,10-dioxo-1,4-anthracenediyl)bis[imino-2,1-ethanediylimino-(1-methylpropyl)-2-oxo-2,1-ethanediyl]]]bis-carbamic acid, bis(1,1-dimethylethyl)ester The general procedure of Example 1 was followed using 3.61 g of N-tertiary butyloxycarbonyl-L-isoleucine hydroxysuccinimide ester in place of the L-alanine ester and appropriate amounts of the other reagents, giving 1.2 g of the desired product, mp >200° C.

EXAMPLE 8

[S-(R*,R*)]-N,N'-[(9,10-Dihydro-5,8-dihydroxy-9,10-dioxo-1,4-anthracenediyl)bis[imino-2,1-ethanediylimino-[2-(methylthio)ethyl]-2-oxo-2,1-ethanediyl)]]]bis-carbamic acid, bis(1,1-dimethylethyl)ester The general procedure of Example 1 was followed using 3.8 g of N-tertiary butyloxycarbonyl-L-methionine hydroxysuccinimide ester in place of the L-alanine ester and appropriate amounts of the other reagents, giving 1.3 g of the desired product, mp 195° C. (dec.).

EXAMPLE 9

[S-(R*,R*)]-5,5'-[(9,10-Dihydro-5,8-dihydroxy-9,10-dioxo-1,4-anthracenediyl)bis(imino-2,1-ethanediylimino)]-bis[4-[[(1,1-dimethylethoxy)carbonyl]amino]-5-oxo-pentanoic acid], bis(1,1-dimethylethyl)ester The general procedure of Example 1 was followed using 50 ml of dry dimethylformamide as solvent and 2.2 g of N-tertiary-butyloxycarbonyl-L-glutamic acid-t-butyl ester, hydroxysuccinimide ester in place of the L-alanine ester and appropriate amounts of the other reagents, giving 1.2 g of the desired product, mp 172° C.(dec.).

EXAMPLE 10

[S-(R*,R*)]-N,N'-[(9,10-Dihydro-5,8-dihydroxy-9,10-dioxo-1,4-anthracenediyl)bis[imino-2,1-ethanediylimino-(1-methylethyl)-2-oxo-2,1-ethanediyl]]]bis-carbamic acid, bis(1,1-dimethylethyl)ester The general procedure of Example 1 was followed using 50 ml of dimethylformamide as solvent and 3.46 g of N-tertiary-butyloxycarbonyl-L-valine hydroxysuccinimide ester in place of the L-alanine ester and appropriate amounts of the other reagents, giving 1.04 g of the desired product, mp >200° C.

EXAMPLE 11

[R-(R*,R*,S*,S*)]-N,N'-[(9,10-Dihydro-5,8-dihydroxy-dioxo-1,4-anthracenediyl)bis[imino-2,1-ethanediylimino[1-(1-hydroxyethyl)-2-oxo-2,1-ethanediyl]]]bis-carbamic acid, bis(1,1-dimethylethyl)ester The general procedure of Example 1 was followed using 50 ml of dry dimethylformamide as solvent and 3.48 g of N-tertiary-butyloxycarbonyl-L-threonine hydroxysuccinimide ester in place of the L-alanine ester and appropriate amounts of the other reagents, giving 2.0 g of the desired product, mp 140° C. (dec.).

EXAMPLE 12

[R-(R*,R*)]-N,N'-[(9,10-Dihydro-5,8-dihydroxy-9,10-dioxo-1,4-anthracenediyl)bis(imino-2,1-ethanediylimino-carbonylethylidene)]bis-carbamic acid, bis(1,1- dimethylethyl)ester The general procedure of Example 1 was followed using 3.15 g of N-tertiary-butyloxycarbonyl-D-alanine hydroxysuccinimide ester and appropriate amounts of the other reagents, giving 900 mg of the desired compound, mp 198° C. (dec.).

Example 13

[S-(R*,R*)]-N,N'-[(9,10-Dihydro-5,8-dihydroxy-9,10-dioxo-1,4-anthracenediyl)bis[imino-2,1-ethanediylimino-(4-hydryphenyl)methyl]-2-oxo-2,1-ethanediyl]]]bis-carbamic acid, bis(1,1-dimethylethyl)ester The general procedure of Example 1 was followed using 50 ml of dry dimethylformamide as solvent, 4.16 g of N-tertiary-butyloxycarbonyl-L-tyrosine hydroxysuccinimide ester and appropriate amounts of the other reagents, giving 1.04 g of the desired compound, mp 160° C. (dec.).

Example 14

[S-(R*,R*)]-N,N'-[(9,10-Dihydro-5,8-dihydroxy-9,10-dioxo-1,4-anthracenediyl)bis[imino-2,1-ethanediylimino-[1-(hydroxymethyl)-2-oxo-2,1-ethanediyl]]]bis-carbamic acid, bis(1,1-dimethylethyl)ester A mixture of 712 mg of 1,4-bis[(2-aminoethyl)-amino]-5,8-dihydroxyanthraquinone base and 136 g of N-tertiary-butyloxycarbonyl-L-serine hydroxysuccinimide ester in 50 ml of dimethylformamide was stirred overnight at 25° C. Evaporation to dryness gave a residue which was triturated with ethyl acetate and ether and dried. It was then washed with cold water and vacuum dried to give 933 mg of the desired product, mp 200° C. (dec.).

Example 15

[(R*,R*)]-N,N'-[(9,10-Dihydro-5,8-dihydroxy-9,10-R-(R* dioxo-1,4-anthracenediyl)bis[imino-2,1-ethanediyl[(2-hydroxyethyl)imino][1-(2-methylpropyl)-2-oxo-2,1-ethane-diyl]]]bis-carbamic acid, bis(1,1-dimethylethyl)ester The general procedure of Example 12 was followed using 1.496 g of N-tertiary-butyloxycarbonyl-D-leucine in place of the L-leucine, giving 822 mg of the desired product, mp 110° C.

EXAMPLE 16

[S-(R*,R*)]-N,N'-[(9,10-Dihydro-5,8-dihydroxy-9,10-dioxo-1,4-anthracenediyl)bis(imino-2,1-ethanediyl)]bis-[2-aminopropanamide], dihydrochloride A 485 mg portion of [S-(R*,R*)]-N,N'-[(9,10-dihydro-5,8-dihydroxy-9,10-dioxo-1,4-anthracenediyl)bis-[imino-2,1-ethanediylimino(1-methyl-2-oxo-2,1-ethanediyl)]]bis-carbamic acid, bis(1,1-dimethylethyl)ester was slurried in 10 ml of glacial acetic acid and 5 ml of anisole was added. Hydrogen chloride gas was bubbled into the solution for 5 minutes with stirring, then the mixture was allowed to stand overnight. The resulting gum was stirred with 30 ml of ether giving a solid which was collected, washed with ether and dried in vacuo at 80° C., 8 mg of the desired product. H.P.L.C. retention time on a Whatman column using water:acetonitrile:-methyl cellosolve:formic acid at the indicated ratio at a flow rate of 2.5 ml/minute here and in future examples. 75:20:2.5:2.5 =209 seconds

EXAMPLE 17

[S-(R*,R*)]-N,N'-[(9,10-Dihydro-5,8-dihydroxy-9,10-dioxo-1,4-anthracenediyl)bis(imino-2,1-ethanediyl)-]bis[2-aminobenzenepropanamide], dihydrochloride A 200 mg portion of [S-(R* ,R*)]-N,N'-[(9,10-dihydro-5,8-dihydroxy-9,10-dioxo-1,4-anthracenediyl)-bis-[imino-2,1-ethanediylimino[2-oxo-1-(phenylmethyl)-2,1-ethanediyl]]]bis-carbamic acid, bis(1,1-dimethylethyl)-ester was reacted as described in Example 16, giving 185 mg of the desired product, H.P.L.C. 60:30:5:5 =230 seconds.

EXAMPLE 18

[S-(R*,R*)]-N,N'-[(9,10-Dihydro-5,8-dihydroxy-9,10-dioxo-1,4-anthracenediyl)bis(imino-2,1-ethanediyl)]bis-[-amino-4-methylpentanamide], dihydrochloride A 1.50 g portion of [S-(R*,R*)]-N,N'-[(9,10-dihydro-5,8-dihydroxy-9,10-dioxo-1,4-anthracenediyl)bis-imino-2,1-ethanediylimino[1-(2-methylpropyl)-2-oxo-2,1-ethanediyl]]]bis-carbamic acid, bis(1,1-dimethylethyl)ester was reacted as described in Example 16, giving 867 mg of the desired product as a blue-black solid, mp 180°–183° C.

EXAMPLE 19

N,N'-[(9,10-Dihydro-5,8-dihydroxy-9,10-dioxo-1,4-anthracenediyl)bis(imino-2,1-ethanediyl)]bis[2-amino-acetamide], dihydrochloride A 1 0 g portion of N,N'-[(9,10-dihydro-5,8-ethanediylimino(2-oxo-2,1-ethanediyl)]]bis-carbamic acid, bis(1,1-dimethylethyl)ester was reacted as described in Example 16, giving 676 mg of the desired product, H.P.L.C. 60:30:5:5 = 96 seconds.

EXAMPLE 20

[(R*,R*)]-N,N'-[(9,10-Dihydro-5,8-dihydroxy-9,10-dioxo-1,4-anthracenediyl)bis(imino-2,1-ethanediyl)]bis-[2-amino-4-methylentanamide], dihydrochloride A 200 mg portion of [R-(R*,R*)]-N,N'-[(9,10-dihydro-5,8-dihydroxy-9,10-dioxo-1,4-anthracenediyl)bis-[imino-2,1-ethanediylimino[1-(2-methylpropyl)-2-oxo-2,1-ethanediyl]]]bis-carbamic acid, bis(1,1-dimethylethyl)ester was reacted as described in Example 16, giving 157 mg of the desired product, H.P.L.C. 60:30:5:5 = 199 seconds.

EXAMPLE 21

[S-(R*,R*,R*,R*)]-N,N'-[(9,10-Dihydro-5,8-dihydroxy-9,10-dioxo-1,4-anthracenediyl)bis(imino-2,1-ethanediyl)]bis-[2-amino-3-methylpentanamide], dihydrochloride A 1.0 g portion of [S-(R*,R*,R*,R*)]-N,N'-[(9,10-dihydro-5,8-dihydroxy-9,10-dioxo-1,4-anthracenediyl)-bis[imino-2,1-ethanediylimino[(1-methylpropyl)-2-oxo-2,1-ethanediyl]]]bis-carbamic acid, bis(1,1-dimethylethyl)ester was reacted as described in Example 16, giving 850 mg of the desired product, H.P.L.C. 60:32:4:4 = 229 seconds.

Example 22

[S-(R*,R*)]N,N'(9,10-Dihydro-5,8-dihydroxy-9,10-dioxo-1,4-anthracenediyl)bis(imino-2,1-ethanediyl)]-bis[2-amino-4-(methylthio)butanamide], dihydrochloride A 500 mg of [S-(R*,R*)]-N,N'-[(9,10-dihydro-5,8-dihydroxy-9,10-dioxo-1,4-anthracenediyl)bis[imino-2,1-ethanediylimino[1-[2-(methylthio)ethyl]-2-oxo-2,1-ethanediyl]]]bis-carbamic acid, bis(1,1-dimethylethyl)ester was reacted as described in Example 16, giving 460 mg of the desired product, H.P.L.C. 60:32:4:4 = 120 seconds.

EXAMPLE 23

[S-(R*,R*)]-5,5'-[(9,10-Dihydro-5,8-dihydroxy-9,10-dioxo-1,4-anthracenediyl)bis(imino-2,1-ethanediylimino)]-bis[4-amino-5-oxo-pentanoic acid], dihydrochloride A 500 mg of [S-(R*,R*)]-5,5'-[(9,10-dihydro-5,8-dihydroxy-9,10-dioxo-1,4-anthracenediyl)bis[imino-2,1-ethanediylimino)]bis[4-[[(1,1-dimethylethoxy)carbonyl]amino]-5-oxo-pentanoic acid]bis(1,1-dimethylethyl)ester was reacted as described in Example 16, giving mg of the desired product, H.P.L.C. 60:32:4:4 = 75 seconds.

EXAMPLE 24

[S-(R*,R*)]-N,N'-[(9,10-Dihydro-5,8-dihydroxy-9,10-dioxo-1,4-anthracenediyl)bis(imino-2,1-ethanediyl)]bis-[2-Amino-3-methylbutanamide], dihydrochloride A 500 mg portion of [S-(R*,R*)]-N,N'-[(9,10-dihydro-5,8-dihydroxy-9,10-dioxo-1,4-anthracenediyl)bis-[imino-2,1-ethanediylimino[1-(1-methylethyl)-2-oxo-2,1-ethanediyl]]]bis-carbamic acid, bis(1,1-dimethylethyl)ester was reacted as described in Example 16, giving 440 mg of the desired product, H.P.L.C. 60:32:4:4 = 118 seconds.

EXAMPLE 25

[R-(R*,R*)]-N,N'-[(9,10-Dihydro-5,8-dihydroxy-9,10-dioxo-1,4-anthracenediyl)bis(imino-2,1-ethanediyl)]bis-[2-aminopropanamide], dihydrochloride A 700 mg portion of [R-(R*,R*)]-N,N'-[(9,10-dihydro-5,8-dihydroxy-9,10-dioxo-1,4-anthracenediyl)bis-(imino-2,1-ethanediyliminocarbonylethylidene)]bis-carbamic acid, bis(1,1-dimethylethyl)ester was reacted as described in Example 16, giving 542 mg of the desired product, H.P.L.C. 70:20:5:5 = 196 seconds.

EXAMPLE 26

[2S-(2R*,2'R*,3S*,3'S*)]-N,N'-[(9,10-Dihydro-5,8-dihydroxy-9,10-dioxo-1,4-anthracenediyl)bis(imino-2,1-ethanediyl)]bis[2-amino-3-hydroxybutanamide]bis(trifluoroacetate)

A 500 mg portion of [R-(R*,R*,S*,S*)]-N,N'-[(9,10-dihydro-5,8-dihydroxy-9,10-dioxo-1,4-anthracenediyl)-bis[imino-2,1-ethanediylimino[1-(1-hydroxyethyl)-2-oxo-2,1-ethanediyl]]]bis-carbamic acid, bis(1,1-dimethylethyl)ester was slurried in 5 ml of anisole, cooled in an ice bath and 10 ml of trifluoroacetic acid was added. The mixture was stirred in the ice bath for 15 minutes, then at room temperature for 1.5 hours and diluted with 50 ml of ether. The solid was collected, washed with ether and dried in vacuo, giving 455 mg of the desired product, H.P.L.C. 60:32:4:4 = 77 seconds.

EXAMPLE 27

[S-(R*,R*)]-N,N'-[(9,10-Dihydro-5,8-dihydroxy-9,10-dioxo-1,4-anthracenediyl)bis(imino-2,1-ethanediyl)]bis [2-amino-N-(2-hydroxyethyl)-4-methylpentanamide]ditrifluoroacetate A 200 mg portion of [S-(R*,R*)]-N,N'-[(9,10-dihydro-5,8-dihydroxy-9,10-dioxo-1,4-anthracenediyl)bis-[imino-2,1-ethanediyl[(2-hydroxyethyl)imino]-1-(2-methylpropyl)-2-oxo-2,1-ethanediyl)]]-carbamic acid, bis(1,1-dimethylethyl)ester was reacted as described in Example 26, giving 302 mg of the desired product, mp 125°–135° C.

EXAMPLE 28

N,N'-[(9,10-Dihydro-5,8-dihydroxy-9,10-dioxo-1,4-anthracenediyl)bis(imino-2,1-ethanediyl)]bis[2-amino-N-(2-hydroxyethyl)-4-methylpentanamide], dihydrochloride A solution of 150 mg of [S-(R*,R*)]-N,N'-[(9,10-dihydro-5,8-dihydroxy-9,10-dioxo-1,4-anthracenediyl)-bis(imino-2,1-ethanediyl)]bis[2-amino-N-(2-hydroxyethyl)-4-methylpentanamide]ditrifluoroacetate in 15 ml of water was percolated slowly through a 20 ml bed of Dower 1×4 Cl⁻ resin. The blue fractions were collected, combined and freeze-dried, giving 95 mg of the desired product, mp 160°–175° C.

EXAMPLE 29

[R-(R*,R*)]-N,N'-[(9,10-Dihydro-5,8-dihydroxy-9,10-dioxo-1,4-anthracenediyl)bis(imino-2,1-ethanediyl)]bis-[2-amino-N-(2-hydroxyethyl)-4-methylpentanamide]-tris(trifluoroacetate)

A 300 mg portion of [R-(R*,R*)]-N,N'-[(9,10-dihydro-5,8-dihydroxy-9,10-dioxo-1,4-anthracenediyl)bis-[imino-2,1-ethanediyl[(2-hydroxyethyl)imino][1-(2-methylpropyl)-2-oxo-2,1-ethanediyl]]]bis-carbamic acid, bis(1,1-dimethylethyl)ester was reacted as described in Example 26, giving 335 mg of the desired product, mp 125°–135° C.

EXAMPLE 30

[S-(R*,R*)]-N,N'-[(9,10-Dihydro-5,8-dihydroxy-9,10-dioxo-1,4-anthracenediyl)bis[imino-2,1-ethanediylimino[1-(2-methylpropyl)-2-oxo-2,1-ethanediyl]]]biscarbamic acid, (phenylmethyl)ester A 1.78 g portion of 1,4-bis[(2-aminoethyl)amino]-5,8-dihydroxyanthraquinone, dihydrochloride and 3.48 ml of triethylamine were slurried in 50 ml of tetrahydrofuran cooled in an ice bath. A solution of 3.72 g of trimethylsilyl chloride in 20 ml of tetrahydrofuran was added dropwise. The mixture was stirred for one hour in the ice bath, then for one hour at room temperature and filtered. To the filtrate was added 4.0 g of carbobenzyloxy-L-leucine hydroxysuccinimide ester. The mixture was stirred overnight and then filtered. The filtrate was passed through a silica pad, then eluted with 500 ml of tetrahydrofuran and the eluent concentrated in vacuo. The residue was slurried in 50 ml of ethyl acetate, the solid collected, washed with ether and dried in vacuo, giving 1.0 g of the desired product, mp 180° C. (dec.).

EXAMPLE 31

[S-(R*,R*)]-N,N'-[(9,10-Dihydro-5,8-dihydroxy-9,10-dioxo-1,4-anthracenediyl)bis(imino-2,1-ethanediyl)-]bis[2-amino-4-methylpentanamide], dihydrobromide A 500 mg portion of [S-(R*,R*)]-N,N'-[(9,10dihydro-5,8-dihydroxy-9,10-dioxo-1,4-anthracenediyl)bis[imino-2,1-ethanediylimino[1-(2-methylpropyl)-2-oxo-2,1e-thanediyl]]]bis-car bamic acid, (phenylmethyl)ester in 10 ml of glacial acetic acid was cooled in an ice bath to just above freezing. Anhydrous hydrogen bromide was bubbled in for 5 minutes, then the mixture was stirred at room temperature overnight. After dilution with 50 ml of ether, the solid was collected, washed with ether and dried in vacuo, giving 460 mg of the desired product, H.P.L.C. 60:32:4:4=161 seconds.

EXAMPLE 32

[S-(R*,R*)]-N,N'-[(9,10-Dihydro-5,8-dihydroxy-9,10-dioxo-1,4-anthracenediyl)bis[imino-2,1-ethanediylimino-(1-oxo-1,2,6-hexanetriyl)]]tetrakis-carbamic acid, tetrakis(phenylmethyl)ester A mixture of 890 mg of 1,4-bis[(2-aminoethyl)amino]-5,8-dihydroxyanthraquinone, dihydrochloride, and 2.8 g of dicarbonylbenzyloxy-L-lysine hydroxysuccinimide ester in 50 ml of dimethylformamide was stirred overnight and then filtered. The insolubles were slurried with 120 ml of dimethylformamide and filtered. The filtrates were combined, concentrated in vacuo and the residue slurried n 150 ml of tetrahydrofuran. The solid was collected, washed with ether and dried in vacuo, giving 1.3 g of the desired product, mp >200° C.

EXAMPLE 33

[S-(R*,R*)]-N,N'-[(9,10-Dihydro-5,8-dihydroxy-9,10-dioxo-1,4-anthracenediyl)bis(imino-2,1-ethanediyl)-]bis[2,6-diaminohexanamide], tetrahydrobromide A 500 mg portion of [S-(R*,R*)]-N,N'-[(9,10-dihydro-5,8-dihydroxy-9,10-dioxo-1,4-anthracenediyl)bis-(imino- 2,1-ethanediylimino(1-oxo-1,2,6-hexanetriyl)]-]tetrakis-carbamic acid, tetrakis(phenylmethyl)ester was reacted as described in Example 31, giving 403 mg of the desired product, H.P.L.C. 60:32:4:4:=65 seconds.

EXAMPLE 34

[R-(R*,R*)]-S,S'-(9,10-Dihydro-5,8-dihydroxy-9,10-dioxo-1,4-anthracenediyl)bis[imino-2,1-ethanediylimino-[3-oxo-[[(2-phenylmethoxy)carbonyl]amino]-3,1-propanediyl]]carbonothioic ac id, O,O'-bis(phenylmethyl)ester The general procedure of example 32 was followed using 2.7 g of N-S-dicarbobenzyloxy-L-cysteine hydroxysuccinimide ester in place of the L-lysine ester, giving 633 mg of the desired product, mp 185° C. (dec.).

EXAMPLE 35

R-(R*,R*)]-N,N'-[(9,10-Dihydro-5,8-dihydroxy-9,10-dioxo-1,4-anthracenediyl)bis(imino-2,1-ethanediyl)-]bis[2-amino-3-mercaptopropanamide], dihydrobromide A 400 mg portion of [R-(R*,R*)]-S,S'-(9,10-dihydro-5,8-dihydroxy-9,10-dioxo-1,4-anthracenediyl)bisimino-2,1-ethanediylimino[3-oxo-2-[[(2-phenylmethoxy)carbonyl]amino]-3,1-prop anediyl] carbonothioic acid, O,O'-bis(phenylmethyl)ester was reacted as described in Example 31, giving 317 mg of the desired product, H.P.L.C. 60:32:4:4=100 seconds.

EXAMPLE 36

[S-(R*,R*)]-N,N'-(9,10-Dihydro-5,8-dihydroxy-9,10-dioxo-1,4-anthracenediyl)bis(imino-2,1-ethanediyl)-]bis[2-amino-3-hydroxyropanamide]bis(trifluoroacetate)

A 700 mg portion of [S-(R*,R*)]-N,N'-[(9,10-dihydro-5,8-dihydroxy-9;10-dioxo-1,4-anthracenediyl)bis-[imino-2,1-ethanediylimino[1-(hydroxymethyl)-2-oxo-2,1-ethanediyl]]]bis-carbamic acid, bis(1,1-dimethylethyl ester) was reacted as described in Example 26, giving 71.2 mg of the desired product, mp 100° C. (dec.).

EXAMPLE 37

[S-(R*,R*)]-N,N'-[(9,10-Dihydro-5,8-dihydroxy-9,10-dioxo-1,4anthracenediyl)bis(imino-2,1-ethanediyl)]bis-[2,-amino-3-(4-hydroxyphenyl)-propanamide, dihydrochloride A 400 mg portion of [S-(R*,R*)]-N,N'-[(9,10-dihydro-5,8-dihydroxy-9,10-dioxo-1,4-anthracenediyl)bis-[imino-2,1-ethanediylimino[1-[(4-hydroxyphenyl)methyl]-2-oxo-2,1-ethanediyl 9 ]]bis-carbamic acid, bis(1,1-dimethylethyl)ester was reacted as described in Example 16, giving the desired product, H.P.L.C. 70:24:3:3=170 seconds.

EXAMPLE 38

[S-R*,R*)]-4,4'-[(9,10-Dihydro-5,8-dihydroxy-D9,10-dioxo-1,4-anthracenediyl)bis(imino-2,1-ethanediylimino)]bis[3-[[9H-fluoren-9-ylmethoxycarbonyl]amino]-4-oxobut anoic acid],bis(1,1-dimethyl)ester A 1.029 g portion of fluorenylmethyloxycarbonyl aspartic acid, β-tertiary butyl ester was slurried in 30 ml of ethyl acetate. A 284 mg portion of N-methylmorpholine was added and the mixture was cooled in an ice-methanol bath. A 382 mg portion of isobutyloxycarbonyl chloride was added, the mixture was stirred for 5 minutes, then 322 mg of N-hydroxysuccinimide in 1 ml of dimethylformamide was added. The mixture was stirred 5 minutes in the cold, then at room temperature overnight, diluted with 50 ml of ethyl acetate, cooled in an ice bath and extracted with two 10 ml portions of ice cooled water. The extracts were combined, dried with sodium sulfate, evaporated to an oil and dissolved in 15 ml of dimethylformamide. This solution was added to a solution of 300 mg of 1,4-bis[(2-aminoethyl)amino]-5,8-dihydroxyanthraquinone in 10 ml of dimethylformamide. This mixture was stirred overnight, then evaporated to dryness, giving 707 mg of [S-(R*,R*)]-4,4'-[(9,10-dihydro-5,8-dihydroxy-9,10-dioxo-1,4-anthracenediyl)bis(imino-2,1-ethanediylimino)]bis[3-[[(9H-fluoren-9-ylmethoxy)carbonyl]amino]-4-oxobutanoic acid]bis(1,1-dimethylethyl)ester.

EXAMPLE 39

[S-(R*,R*)]-4,4'-[(9,10-Dihydro-5,8-dihydroxy-9,10-dioxo-1,4-anthracenediyl)bis(imino-2,1-ethanediylimino)]bis[3-amino-4-oxobutanoic acid]bis(1,1-dimethylethyl)ester A 350 mg portion of the product of Example 38 was dissolved in 20 ml of dimethylformamide. Dimethylamine was bubbled into the solution for 5 minutes, then the mixture was evaporated to dryness, triturated with ether and dried, giving 208 mg of the desired product, mp 140° C. (dec.).

EXAMPLE 40

S-(R*,R*)]-4,4'-[(9,10-Dihydro-5,8-dihydroxy-9,10-dioxo-1,4-anthracenediyl)bis(imino-2,1-ethanediylimino)]bis[3amino-4-oxobutanoic acid]bis(trifluoroacetate)

A 100 mg portion of [S-(R*,R*)]-4,4'-[(9,10-dihydro-5,8-dihydroxy-9,10-dioxo-1,4-anthracenediyl)bis(imino-2,1-ethanediylimino)]bis[3-amino-4-oxobutanoic acid]-bis(1,1-dimethylethyl)ester was reacted as described in Example 26, giving 88 mg of the desired product, mp 125° C. (dec.).

EXAMPLE 41

S-(R*,R*)]-N,N'-[(9,10-Dihydro-5,8-dihydroxy-9,10-dioxo-1,4-anthracenediyl)bis[imino-2,1-ethanediylimino-[2-oxo-1-[(phenylmethoxy)methyl]-2,1-ethanediyl]]]biscarbamic acid, bis(1, 1-dimethylethyl)ester A 1.823 g portion of N-butyloxycarbonyl-O-benzyl-L-serine hydroxysuccinimide ester and 712 mg of 1,4-bis[(2-aminoethyl)amino]-5,8-dihydroxyanthraquinone, in 50 ml of dimethylformamide was stirred overnight, then evaporated to dryness and triturated with acetone and ether. The solid was collected, washed with water and dried, giving 1.054 g of the desired product, mp 150° C.

EXAMPLE 42

[S-(R*,R*)]-N,N'-[(9,10-Dihydro-5,8-dihydroxy-9,10-dioxo-1,4-anthracenediyl)bis[imino-2,1-ethanediyl)-]bis[2-amino-3-(phenylmethoxy)-propanamide]bis(trifluoroacetate)

A 250 mg portion of [S-(R*,R*)]-N,N'-[(9,10-dihydro-5,8-dihydroxy-9,10-dioxo-1,4-anthracenediyl)-bisimino-2,1-ethanediylimino[2-oxo-1-[(phenylmethoxy)methyl]-2,1-ethanediyl]]]bis-carbamic acid, bis(1,-1dimethylethyl)ester was reacted as described in Example 26, giving 252 mg of the desired product, mp 110° C. (dec.).

EXAMPLE 43

[S-(R*,R*)]-5,5'-(9,10-Dihydro-5,8-dihydroxy-9,10-dioxo-1,4-anthracenediyl)bis(imino-2,1-ethanediylimino)]bis[4-[[(1,1-dimethylethoxy)carbonyl]amino]-5-oxopentanoic acid]bis(phenylmethyl)ester A 712 mg portion of 1,4-bis[(2-aminoethyl)amino]-5,8-dihydroxyanthraquinone and 1.91 g of N-butyloxycarbonyl-γ-O-benzyl-L-glutamic acid hydroxysuccinimide ester in 50 ml of dimethylformamide was stirred overnight, then evaporated to dryness, triturated with 100 ml of acetone, filtered and evaporated, giving 952 mg of the desired product, mp 185°–190°C. (dec.).

EXAMPLE 44

[S-(R*,R*)]-5,5'-[(9,10-Dihydro-5,8-dihydroxy-9,10-dioxo-1,4-anthracenediyl)bis(imino-2,1-ethanediylimino)]bis[4-amino-5-oxopentanoic acid]bis(phenylmethyl)ester, bis(trifluoroacetate)

A 500 mg portion of [S-(R*,R*)]-5,5'-[(9,10-dihydro-5,8-dihydroxy-9,10-dioxo-1,4-anthracenediyl)bis(imino-2,1-ethanediylimino)]bis[4-[[(1,1-dimethylethoxy)carbonyl]amino]-5-oxopentanoic acid]bis(phenylmethyl)ester was reacted as described in Example 26, giving 488 mg of the desired product, mp 110° C. (dec.).

EXAMPLE 45

[S-(R*,R*)]-4,4'-[(9,10-Dihydro-5,8-dihydroxy-9,10-dioxo-1,4-anthracenediyl)bis(imino-2,1-ethanediylimino)]bis[3-[[(1,1-dimethylethoxy)carbonyl]amino]-4-oxobutanoic acid]bis(phenylmethyl)ester The general procedure of Example 43 was followed, using 1.85 g of N-butyloxycarbonyl-β-O-benzyl-L-aspartic acid hydroxysuccinimide ester in place of the L-glutamic acid ester, giving 713 mg of the desired product, mp 185° C. (dec.).

EXAMPLE 46

[S-(R*,R*)]-4,4'-[(9,10-Dihydro-5,8-dihydroxy-9,10-dioxo-1,4-anthracenediyl)bis(imino-2,1-ethanediylimino)]bis[3-amino-4-oxobutanoic acid]bis(phenylmethyl)ester, bis(trifluoroacetate)

A 500 mg portion of [S-(R*,R*)]-4,4'-[(9,10-dihydro-5,8-dihydroxy-9,10-dioxo-1,4-anthracenediyl)bis(imino-2,1-ethanediylimino)]bis[3-[[(1,1-dimethoxy)carbonyl]amino]-4-oxo butanoic acid]bis(phenylmethyl)ester was reacted as described in Example 26, giving 494 mg of the desired product, mp 150° C. (dec.).

EXAMPLE 47

[S-(R*,R*)]-5,5'-[(9,10-Dihydro-5,8-dihydroxy-9,10-dioxo-1,4-anthracenediyl)bis(imino-2,1-ethanediylimino)]bis[5-oxo-4-[[(phenylmethoxy)carbonyl]amino]pentanoic acid], bis(1,1-dimethylethyl)ester A mixture of 712 mg of 1,4-bis[(2-aminoethyl)amino]-5,8-dihydroxyanthraquinone and 1.91 g of N-carbobenzyloxy-L-glutamic acid γ-O-t-butyl ester hydroxysucinimide ester in 50 ml of dimethylformamide was stirred of 30 ml of acetone and 30 ml of ether. The solid was collected, washed with ether and dried, giving 1.19 g of the desired product, mp 175°–185° C. (dec.).

EXAMPLE 48

[S-(R*,R*)]-5,5'-[(9,10-Dihydro-5,8-dihydroxy-9,10-dioxo-1,4-anthracenediyl)bis(imino-2,1-ethanediylimino)]bis[5-oxo-4-[[(phenylmethoxy)carbonyl]amino]pentanoic acid, bis(trifluoroacetate)

A 300 mg portion of [S-(R*,R*)]-5,5'-[(9,10-dihydro-5,8-dihydroxy-9,10-dioxo-1,4-anthracenediyl)bis(imino-2,1-ethanediylimino)]bis[5-oxo-4-[[(phenylmethoxy)carbonyl]amino]pentanoic acid], bis(1,1-dimethylethyl)ester was reacted as described in Example 26, giving 80 mg of the desired product, mp 200° C. (dec.).

EXAMPLE 49

N,N'-(9,10-Dihydro-5,8-dihydroxy-9,10-dioxo-1,4-anthracenediyl)bis(imino-2,1-ethanediyl)]-[N-[(phenylmethoxy)carbonyl]-L-leucyl-L-alaninamide]

A mixture of 36 mg of 1,4-bis[(2-aminoethyl)amino]-5,8-dihydroxyanthraquinone and 100 mg of N-carbobenzyloxy-L-leucyl-L-alanyl hydroxysuccinimide ester in 2.5 ml of dimethylformamide was stirred overnight, then evaporated to dryness. The residue was slurried in 100 ml of methanol, filtered, slurried in 10 ml of water at pH 1.8 for ½ hour, collected by filtration and dried. The residue was slurried in ethyl acetate, then evaporated to dryness, giving 48 mg of the desired product, mp>220° C.

EXAMPLE 50

N,N'-[(9,10-Dihydro-5,8-dihydroxy-9,10-dioxo-1,4-anthracenediyl)bis(imino-2,1-ethanediyl)]bis[L-leucyl-L-alaninamide], dihydrobromide A 34 mg portion of N,N'-[(9,10-dihydro-5,8-dihydroxy-9,10-dioxo-1,4-anthracenediyl)bis(imino-2,1-ethanediyl)][N-[(phenylmethoxy)carbonyl]-L-leucyl-L-alaninamide]in 5 ml of glacial acetic acid saturated with hydrogen bromide was stirred overnight, precipitated with ether, collected and dried, giving 32 mg of the desired product, mp 200° C. (dec.).

EXAMPLE 51

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]-L-leucyl-L-alanyl-L-leucinamide A mixture of 199 mg of [S-(R*,R*)]-N,N'(9,10-dihydro-5,8-dihydroxy-9,10-dioxo-1,4-anthracenediyl)bis(imino-2,1-ethanediyl)]bis[2-amino-4-methylpentanamide]dihydrobromide, 229 mg of carbobenzyloxy-L-leucyl-L-alanyl hydroxysuccinimide ester and 0.2 ml of triethylamine in 10 ml of dimethylformamide was stirred overnight and then evaporated to dryness. The residue was triturated with ethyl acetate and then filtered. The filtrate was washed twice with a mixture of 50 ml of 0.1 N hydrochloric acid and 50 ml of water, then evaporated giving 225 mg of the desired product, mp>250° C.

EXAMPLE 52

N,N'-[(9,10-Dihydro-5,8-dihydroxy-9,10-dioxo-1,4-anthracenediyl)bis(imino-2,1-ethanediyl)]bis[L-leucyl-L-Alanyl-L-leucinamide]dihydrobromide A 75 mg portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]-L-leucyl-L-alanyl-L-leucinamide was reacted as described in Example 31, giving 68 mg of the desired product, mp 195° C. (dec.).

EXAMPLE 53

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]glycyl-L-phenylalaninamide A 7.17 g portion of carbobenzyloxy glycyl-L-phenylalanine and 2.30 g of N-hydroxysuccinimide were slurried in 100 ml of acetonitrile, cooled in an ice bath, with the addition of 5 ml of dimethylformamide, to obtain solution. A precooled solution of 4.12 g of dicyclohexylcarbodiimide in 50 ml of acetonitrile was added dropwise. The mixture was stirred in the ice bath for 2 hours, then refrigerated overnight, filtered and the filtrate concentrated in vacuo. The residue was taken up in 125 ml of ethyl acetate, washed with precooled 5% aqueous sodium bicarbonate, then twice with water, dried and concentrated in vacuo. The residue was dissolved in 125 ml of 2-propanol and refrigerated overnight. The resulting gum was taken up in tetrahydrofuran and concentrated in vacuo, giving 6.5 g of 1-[[N-[N-[(phenylmethoxy)carbonyl]glycyl]-L-phenylalanyl]oxy]-2,5-pyrrolidinedione.

A mixture of 2.4 g of the above ester was reacted as described in Example 32, giving 560 mg of the desired product, mp>200° C.

EXAMPLE 54

[S-(R*,R*)]-N,N'-[(9,10-Dihydro-5,8-dihydroxy-9,10-dioxo-1,4-anthracenediyl)bis(imino-2,1-ethanediyl)-]bis[glycyl-L-phenylalaninamide]dihydrobromide A 250 mg portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]glycyl-L-phenylalaninamide was reacted as described in Example 31, giving 238 mg of the desired product, H.P.L.C. 60:32:4:4=261 seconds.

EXAMPLE 55

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]-L-alanyl-glycinamide A 2.8 g portion of carbobenzyloxy-L-alanylglycine was reacted as described in Example 53, giving 850 mg of 1-[[N-[N-[(phenylmethoxy)carbonyl]-L-alanyl]-glycyl]oxy]-2,5-pyrrolidinedione.

A 415 mg portion of the above ester was reacted as described in Example 32, giving 161 mg of the desired product as a gum.

EXAMPLE 56

N,N'-[(9,10-Dihydro-5,8-dihydroxy-9,10-dioxo-1,4-anthracenediyl)bis(imino-2,1-ethanediyl)]bis[L-alanyl-glycinamine]dihydrobromide A 100 mg portion of N,N'-[(9,10-dihydro-5,8 dihydroxy-9,10-dioxo-1,4-anthracenediyl)bis(imino-2,1-ethanediyl)]bis[N-[(phenylmethoxy)carbonyl]-L-alanylglycinamide was reacted as described in Example 31, giving the desired product, H.P.L.C. 70:24:3:3=138 seconds.

EXAMPLE 57

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]glycyl]glycinamide A 7.98 g portion of carbobenzyloxy glycylglycine was reacted as described in Example 53, giving 6.15 g of 1-[[N-[N-[(phenylmethoxy)carbonyl]glycyl]glycyl]oxy]-2,5-pyrrolidinedione.

A 4.18 g portion of the above ester was reacted as described in Example 51, giving 3.4 g of the desired product, mp 155° C. (dec.).

EXAMPLE 58

N,N'-[(9,10-Dihydro-5,8-dihydroxy-9,10-dioxo-1,4-anthracenediyl)bis(imino-2,1-ethanediyl)]bis[glycyl-glycinamide]dihydrobromide A 3 g portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]glycyl]-glycinamide was reacted as described in Example 31, giving 3.4 g of the desired product, mp 100° C. (dec.).

EXAMPLE 59

N,N'-[(9,10-Dihydro-5,8-dihydroxy-9,10-dioxo-1,4-anthracenediyl)bis(imino-2,1-ethanediyl)]bis[N-[(1,1-dimethylethoxy)carbonyl]glycylglycyl]glycinamide A mixture of 2.6 g of N,N'-[(9,10-dihydro-5,8-dihydroxy-9,10-dioxo-1,4-an.thracenediyl)bis(imino-2,1-ethanediyl)]bis[glycylglycinamide]dihydrobromide, 1.8 g of tertiary butyloxycarbonyl glycine hydroxysuccinimide ester and 2.6 ml of triethylamine in 100 ml of dimethylformamide was stirred for 2 days, then evaporated to dryness. The residue was triturated with ethyl acetate, filtered and dried in vacuo. This residue was triturated in 100 ml of cold water at pH 3 for ½ hour, then filtered and the solid dried, giving 1.8 g of the desired product, mp 165° C.

EXAMPLE 60

N,N'-[(9,10-Dihydro-5,8-dihydroxy-9,10-dioxo-1,4-anthracenediyl)bis(imino-2,1-ethanediyl)]bis[glycylglycyl glycinamide]bis(trifluoroacetate)

A 1.5 g portion of N,N'-[(9,10-dihydro-5,8-dihydroxy-9,10-dioxo-1,4-anthracenediyl)bis(imino-2,1-ethanediyl)]bis[N-[(dimethylethoxy)carbonyl]glycyl-glycyl]glycinamide was reacted as described in Example 26, giving 1.69 g of the desired product, mp 100°–113° C.

EXAMPLE 61

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]glycyl-L-prolyl-L-leucyl-glycyl]-L-prolinamide A 158 mg portion of carbobenzyloxy glycyl-L-prolyl-L-leucyl-glycyl-L-proline was reacted as described in Example 53, giving 150 mg of the desired product, mp 150° C. (dec.).

EXAMPLE 62

N,N'-[(9,10-Dihydro-5,8-dihydroxy-9,10-dioxo-1,4-anthracenediyl)bis(imino-2,1-ethanediyl)]bis[glycyl-L-prolyl-L-leucylglycyl-L-prolinamide]dihydrobromide A 100 mg portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]glycyl-L-prolyl-L-leucylglycyl]-L-prolinamide was reacted as described in Example 31, giving 74 mg of the desired product, =4 215 seconds. H.P.L.C. 60:32:4

EXAMPLE 63

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]glycyl-L-prolylglycylglycyl-L-prolyl]-L-alaninamide A 152 mg portion of carbobenzyloxy-glycyl-L-prolyl-glycylglycyl-L-prolyl-L-alanine was reacted as described in Example 53, giving 140 mg of the desired product, mp 165° C. (dec.).

EXAMPLE 64

N,N'-[(9,10-Dihydro-5,8-dihydroxy-9,10-dioxo-1,4-anthracenediyl)bis(imino-2,1-ethanediyl)]bis[glycyl-L-prolylglycylglycyl-L-prolyl-L-alaninamide]-dihydrobromide An 80 mg portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]-glycyl-L-prolylglycylglycyl-L-prolyl]-L-alaninamide was reacted as described in Example 31, giving 48 mg of the desired product, H.P.L.C. 60:32:4:4=103 seconds.

EXAMPLE 65

N,N'-[(9,10-Dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-leucinamide A mixture of 3.25 g of [S-(R*,R*)]-N,N'-[(9,10-dihydro-5,8-dihydroxy-9,10-dioxo-1,4-anthracenediyl)bis-(imino-2,1-ethanediyl)]bis[2-amino-4-methylpentanamide]ditrifluoroacetate, 3.45 m 1 of triethylamine and 125 ml of dimethylformamide was stirred and 2.52 g of N-tertiary brtyloxycarbonyl-L-alanine hydroxysuccinimide ester was added. The mixture was stirred overnight, then evaporated to dryness, washed with 500 ml of ethyl acetate, air-dried and washed then with 250 ml of water. The solid was collected, giving 2.3 g of the desired product, mp 215° C. (dec.).

EXAMPLE 66

N,N'-[(9,10-Dihydro-5,8-dihydroxy-9,10-dioxo-1,4-anthracenediyl)bis(imino-2,1-ethanediyl)]bis[L-alanyl-L-leucinamide]bis(trifluoroacetate)

A 2 g portion of N,N'-[(9,10-dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-leucinamide] was reacted as described in Example 26, giving 2.05 g of the desired compound, mp 185° C. (dec.).

EXAMPLE 67

N,N'-[(9,10-Dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-alanyl-L-leucinamide]

A 953 mg portion of N,N'-[(9,10-dihydroxy-9,10-dioxo-1,4-anthracenediyl)bis(imino-2,1-ethanediyl)]bis[L-alanyl-L-leucinamide]bis(trifluoroacetate) and 630 mg of N-tertiary-butyloxycarbonyl-L-alanine hydroxysuccinimide ester were reacted as described in Example 65, giving 907 mg of the desired product, mp>220° C.

EXAMPLE 68

N,N'-](9,10-Dihydro-5,8-dihydroxy-9,10-dioxo-1,4-anthracenediyl)bis(imino-2,1-ethanediyl)]bis[L-alanyl-L-alanyl-L-leucinamide]bis(trifluoroacetate)

A 700 mg portion of N,N'-[(9,10-dihydroxy-9,10-dioxo-1,4-anthracenediyl)bis(imino-2,1-ethanediyl)]bis[N-[(1,1-dimethylethoxy)carbonyl]-L-alanyl-L-alanyl-L-leucinamide]was reacted as described in Example 26, giving 860 mg of the desired product, mp>210° C.

EXAMPLE 69

N,N'-[(9,10-Dihydro-5,8-dihydroxy-9,10-dioxo-1,4-anthracenediyl)bis(imino-2,1-ethanediyl)]bis[N-[(phenylmethoxy)carbonyl]glycylglycyl-L-leucinamide]

A 1.23 g portion of [S-(R*,R*)]-N,N'(9,10-dihydro-5,8-dihydroxy-9,10-dioxo-1,4-anthracenediyl)bis(imino-2,1-ethanediyl)]bis[2-amino-4-methylpentanamide]bis(trifluoroacetate) and 1.19 g of carbobenzyloxyglycylglycyl-hydroxysuccinimide ester were reacted as described in Example 65, giving 1.28 g of the desired compound, mp 197° C. (dec.).

EXAMPLE 70

N,N'-[(9,10-Dihydro-5,8-dihydroxy-9,10-dioxo-1,4-anthracenediyl)bis(imino-2,1-ethanediyl)]bis[glycylglycyl-L-leucinamide]dihydrobromide A 1 g portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]glycylglycyl-L-leucinamide] was reacted as described in Examp le 31, giving 1.01 g of the desired product, mp 189° C. (dec.).

EXAMPLE 71

N,N'-[(9,10-Dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-alanine]

A 2.4 g portion of [(S-(R*,R*)]-N,N'-[(9,10-dihydro-5,8-dihydroxy-9,10-dioxo-1,4-anthracenediyl)bis(imino-2,1-ethanediyl)]bis[2-aminopropanamide]bis(trifluoroacetate) and 2.07 g of N-tertiary-butyloxycarbonyl-L-alanine hydroxysuccinimide ester were reacted as described in Example 65, gibing 1.8 g of the desired product, mp>200° C. (dec.).

EXAMPLE 72

N,N'-[(9,10-Dihydro-5,8-dihydroxy-9,10-dioxo-1,4-anthracenediyl)bis(imino-2,1-ethanediyl)]bis[L-alanyl-L-alanine]bis(trifluoroacetate)

A 1.5 g portion of N,N'-[(9,10-dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-alanine] was reacted as described in Example 26, giving 1.52 g of the desired product, mp 175° C. (dec.).

EXAMPLE 7.

N,N'-[(9,10-Dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-alanyl-L-alanine]

An 870 mg portion of N,N'-[(9,10-dihydro-5,8-dihydroxy-9,10-dioxo-1,4-anthracenediyl)bis(imino-2,1-ethanediyl)]bis[L-alanyl-L-alanine]bis(trifluoroacetate) and 629 mg of N-tertiary-butyloxycarbonyl-L-alanine hydroxysuccinimide ester were reacted as described in Example 65, giving 890 mg of the desired product, mp>200° C. (dec.).

EXAMPLE 73

N,N'-[(9,10-Dihydro-5,8-dihydroxy-9,10-dioxo-1,4-anthracenediyl)bis(imino-2,1-ethanediyl)]bis[L-alanyl-L-alanyl-L-alanine]bis(trifluoroacetate)

A 600 mg portion of N,N'-[(9,10-dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-alanyl-L-alanine] was reacted as described in Example 26, giving 614 mg of the desired product, mp 190° C. (dec.).

EXAMPLE 75

N,N'-[(9,10-Dihydro-5,8-dihydroxy-9,10-dioxo-1,4-anthracenediyl)bis(imino-2,1-ethanediyl)]bis[N-[(1,1-dimethylethoxy)carbonyl]-L-seryl-L-alaninamide A 727 mg portion of [S-(R*,R*)]-N,N'-[(9,10-dihydro-5,8-dihydroxy-9D,10-dioxo-1,4-anthracenediyl)bis-(imino-2,1-ethanediyl)]bis[2-aminopropanamide]bis(trifluoroacetate) and 665 mg of N-tertiarybutyloxycarbonyl-L-serine hydroxysuccinimide ester were reacted as described in Example 65, giving 619 mg of the desired product mp>220° C. (dec.).

EXAMPLE 76

N,N'-[(9,10-Dihydro-5,8-dihydroxy-9,10-dioxo-1,4-anthracenediyl)bis(imino-2,1-ethanediyl)]bis[L-seryl-L-alaninamide]bis(trifluoroacetate)

A 419 mg portion of N,N'-[(9,10-dihydro-5,8-dihydroxy-9,10-dioxo-1,4-anthracenediyl)bis(imino-2,1-ethanediyl)]bis[N-[(1,1-dimethylethoxy)carbonyl]-L-seryl-L-alaninamide]was reacted as described in Example 26, giving 386 mg of the desired product, mp 130° C. (dec.).

EXAMPLE 77

N,N'-[(9,10-Dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-seryl-L-alaninamide]bis(1,1-di methylethyl)ester A 300 mg portion of N,N'-[(9,10-dihydro-5,8-dihydroxy-9,10-dioxo-1,4-anthracenediyl)bis(imino-2,1-ethanediyl)]bis[L-seryl-L-alaninamide]bis(trifluoroacetate) and 0.75 mmole of N-[(9H-fluoren-9-ylmethoxy)carbonyl]-L-α-aspartic acid hydroxysuccinimide ester, γ-O-(1,1-dimethylethyl)ester (prepared as in Example 38) were reacted as described in Example 38, giving 363 mg of the desired product, mp 195 °C. (dec.).

EXAMPLE 78

N,N'-[(9,10-Dihydro-5,8-dihydroxy-9,10-dioxo-1,4-anthracenediyl)bis(imino-2,1-ethanediyl)]bis[L-α-aspartyl-L-seryl-L-alaninamide]bis(1,1-dimethylethyl)ester A 300 mg portion of N,N'-[(9,10-dihydro-5 dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-seryl-L-alaninamide]bis(1,1-dimethylethyl)ester was reacted with dimethylamine-dimethylformamide as described in Example 39, giving 207 mg of the desired product, mp 180° C. (dec.).

EXAMPLE 79

N,N'-[(9,10-Dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-alanyl-L-alaninamide]bis(1,1-dimethylet hyl)ester A 1.74 g portion of N,N'-[(9,10-dihydro-5,8-dihydroxy-9,10-dioxo-1,4-anthracenediyl)bis(imino-2,1-ethanediyl)]bis[L-alanyl-L-alanine]bis(trifluoroacetate) and 4.4 mmole of N-[(9H -fluoren-9-ylmethoxy)carbonyl]-L-α-aspartic acid hydroxysuccinimide ester, γ-O-(1,1-dimethyl- ethyl)ester (prepared as in Example 38) were reacted as described in Example 38, giving 2.28 g of the desired product, mp 215° C. (dec.).

EXAMPLE 80

N,N'-[(9,10-Dihydro-5,8-dihydroxy-9,10-dioxo-1,4-anthracenediyl)bis(imino-2,1-ethanediyl)]bis[L-α-aspartyl-L-alanyl-L-alaninamide]bis(1,1-dimethylethyl)ester A 500 mg portion of N,N'-[(9,10-dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-alanyl-L-alaninamide]bis(1,1-dimethylethyl)ester was reacted with dimethylamine-dimethylformamide as described in Example 39, giving 317 mg of the desired product, mp 208° C. (dec.).

EXAMPLE 81

N,N'-[(9,10-Dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-alanyl-L-leucinamide]bis(1,1-dimethylethyl)ester A 1.9 g portion of N,N'-[(9,10-dihydro-5,8-dihydroxy-9,10-dioxo-1,4-anthracenediyl)bis(imino-2,1-ethanediyl)]bis[L-alanyl-L-leucinamide]bis(trifluoroacetate) and 4.4 mmole of N-[(9H-fluoren-9-ylmethoxy)carbonyl-L-γ-aspartic acid hydroxysuccinimide ester, α-O-(1,1-dimethylethyl)ester (prepared as in Example 38) were reacted as described in Example 38, giving 2.6 g of the desired product, mp 200° C. (dec.).

EXAMPLE 82

N,N'-[(9,10-Dihydro-5,8-dihydroxy-9,10-dioxo-1,4-anthracenediyl)bis(imino-2,1-ethanediyl)]bis[L-α-aspartyl- L-alanyl-L-leucinamide]bis(1,1-dimethylethyl)ester A 1 g portion of N,N'-[(9,10-dihydro-5,8-dihydroxy-9,10-dioxo-1,4-anthracenediyl)bis(imino-2,1-ethanediyl)]bis[N[(9H-fluoren-9-ylmethoxy)carbonyl]-L-α-aspartyl-L-alanyl-L-leucinamide]bis(1,1-dimethylethyl)ester was reacted with dimethylamine-dimethylformamide as described in Example 39, giving 607 mg of the desired product, mp 210°0 C. (dec.).

EXAMPLE 83

N,N'-(9,10-Dihydro-5,8-dihydroxy-9,10-dioxo-1,4-anthracenediyl)bis(imino-2,1-ethanediyl)]bis[L-α-aspartyl-L-alanyl-L-alaninamide]bis(trifluoroacetate)

A 100 mg portion of N,N'-[(9,10-dihydro-5,8-dihydroxy-9,10-dioxo-1,4-anthracenediyl)bis(imino-2,1-ethanediyl)]bis[L-a-aspartyl-L-alanyl-L-alaninamide]-bis(1,1-dimethylethyl)ester was reacted as described in Example 26, giving 81 mg of the desired product, mp 153° C. (dec.).

EXAMPLE 84

N,N'-[(9,10-Dihydro-5,8-dihydroxy-9,10-dioxo-1,4-anthracenediyl)bis(imino-2,1-ethanediyl)]bis[L-α-aspartyl-L-alanyl-L-leucinamide]bis(trifluoroacetate)

A 100 mg portion of N,N'-[(9,10-dihydro-5,8-dihydroxy-9,10-dioxo-1,4-anthracenediyl)bis(imino-2,1-ethanediyl)]bis[L-α-aspartyl-L-alanyl-L-leucinamide]-bis(1,1-dimethylethyl)ester was reacted as described in Example 26, giving 86 mg of the desired product, mp 160° C. (dec.).

EXAMPLE 85

N,N'-[(9,10-Dihydro-5,8-dihydroxy-9,10-oxo-1,4-anthracenediyl)bis(imino-2,1-ethanediyl) ]bis[L-arginine(phenylmethyl)]ester, dihydrobromide A 1 g portion of α-carbobenzyloxy-L-arginine hydrobromide and 398 mg of hydroxybenzotriazole were dissolved in 10 ml of dimethylformamide chilled in a methanol-ice bath over 15 minutes. A 536 mg portion of dicyclohexylcarbodiimide was dissolved in a few ml of dimethylformamide and added to the mixture. The mixture was stirred one hour at 0° C., then one hour at room temperature, then filtered and the filtrate added to a solution of 338 mg of 1,4-bis[(2-aminoethyl)amino]-5,8-dihydroxyanthraquinone in dimethylformamide. This mixture was stirred overnight, then evaporated and the residue triturated with ethyl acetate, giving 1.08 g of product, Rf 0.52 in a 3:1:1 (butanol:acetic acid:water) tlc system, mp 120° C. (dec.).

EXAMPLE 86

N,N'-[(9,10-Dihydro-5,8-dihydroxy-9,10-dioxo-1,4-anthracenediyl)bis(imino-2,1-ethanediyl)]-L-arginine, dihydrobromide A 900 mg portion of the compound of Example 85 was dissolved in 25 ml of glacial acetic acid saturated with hydrogen bromide, stirred for 1.5 hours, then quenched in ether and the solid collected and dried to yield 571 mg of crude product, 300 mg of which was resubjected to glacial acetic acid-saturated hydogen bromide for 0.5 hour to yield 250 mg of product, Rf 0.1 in a tetrahydrofuran:water:acetic acid 13:2:1 tlc system.

EXAMPLE 87

N,N'-[(9,10-Dihydro-5,8-dihydroxy-9,10-dioxo-1,4-anthracenediyl)bis(imino-2,-ethanediyl)]bis[L-alanyl-L-arginine]bis(1,1-dimethylethyl)ester, dihydrobromide A 100 mg portion of the compound of Example 86 was dissolved in dimethylformamide and to it was added a solution of 63 mg of N-tertiary-butyloxycarbonyl-L-alanine hydroxysuccinimide ester and 0.086 ml of triethylamine in dimethylformamide. This mixture was stirred overnight, then evaporated and the residue triturated with ethyl acetate, giving 108 mg of product with an Rf of 0.75 in the tlc system of Example 86.

EXAMPLE 88

N,N'-[(9,10-Dihydro-5,8-dihydroxy-9,10-dioxo-1,4-anthracenediyl)bis(imino-2,1-ethanediyl)]bis-[L-alanyl-L-argininamide]tetrahydrobromide A 1.55 g portion of the compound, prepared as described in Example 87, was reacted as described in Example 26, giving 1.2 g of the desired product, Rf 0.5 in tlc system A (dimethylformamide:methyl cellosolve:tetrahydrofuran:isopropanol:acetonitrile:ammonium hydroxide:acetic acid 4:3:3:2:2:1:1).

EXAMPLE 89

N,N'-[(9,10-Dihydro-5 8-dihydroxy-9,10-dioxo-1,4-anthracenediyl)bis(imino-2,1-ethanediyl)]bis[N-[(1,1-dimethylethoxy)carbonyl]-L-alanyl-L-alanyl-L-argininamide]-dihydrobromide A 1.0 g portion of N,N'-[(9,10-dihydro-5,8-dihydroxy-9,10-dioxo-1,4-anthracenediyl)bis (imino-2,1-ethanediyl)]bis[L-alanyl-L-argininamide]dihydrobromide ditrifluoroacetate was dissolved in 90 ml of dimethylformamide. A 0.69 ml portion of triethylamine was added, then 500 mg of N-tertiary butyloxycarbonyl-L-alaninehydroxysuccinimide ester. The mixture was stirred overnight then evaporated. The residue was triturated with ethyl acetate, then with acetone, filtered and dried in vacuo, giving 880 mg of the desired product, mp 200° C. (dec.).

EXAMPLE 90

N,N'-[(9,10-Dihydro-5,8-dihydroxy-9,10-dioxo-1,4-anthracenediyl)bis(imino-2,1-ethanediyl)]bis[L-alanyl-L-alanyl-L-argininamide], dihydrobromide, bis(trifluoroacetate)

A 290 mg portion of N,N'-[(9,10-dihydro-5,8-dihydroxy-9,10-dioxo-1,4-anthracenediyl)bis(imino-2,1-ethanediyl)]bis[N-[(1,1-dimethylethoxy)carbonyl]-L-alanyl-L-alanyl-L-argininamide]dihydrobromide was slurried in 2.9 ml of anisole for 10 minutes in an ice bath. A 5.8 ml portion of trifluoroacetic acid was added, the mixture was stirred for 75 minutes, then quenched in 500 ml of ether. The mixture was filtered and dried in vacuo, giving 254 mg of the desired product, Rf 0.65 (system A, as given in Example 88).

EXAMPLE 91

[S-(R*,R*)][(9,10-Dihydro-5,8-dihydroxy-9,10-dioxo-1,4-anthracenediyl)bis[1-[3-[[imino(nitroamino)methyl]amino]propyl]-2-oxo-2,1-ethanediyl]]bis-carbamic acid, bis(phenylmethyl)ester $N^5$-[Imino(nitroamino)methyl]-$N^2$-[(phenylmethoxy)carbonyl]-L-ornithine, pentachlorophenyl ester was prepared according to J. Org. Chem., 32, 3696 (1976).

A 722 mg portion of the above ester in 5 ml of dimethylformamide was added to a solution of 186 mg of 1,4-bis[(2-aminoethyl)amino]-5,8-dihydroxyanthraquinone in 40 ml of dimethylformamide. This mixture was stirred overnight, then evaporated to dryness. The residue was added to 20 ml of water acidified to pH 1.8 with 1N hydrochloric acid, stirred for 15 minutes and then the solid was collected, washed with water and dried in vacuo, giving 30 mg of the desired product, mp 138° C. (dec.).

EXAMPLE 92

N,N'-[(9,10-Dihydro-5,8-dihydroxy-9,10-dioxo-1,4-anthracenediyl)bis(imino-2,1-ethanediyl)]bis[2-amino-5-[[imino(nitroamino)methyl]amino]pentanamide], tetrahydrobromide To a 100 mg portion of [S-(R*,R*)][(9,10-dihydro-5,8S-dihydroxy-9,10-dioxo-1,4-anthracenediyl)bis[1-[3-[[imino(nitroamino)methyl]amino]propyl]-2-oxo-2,1-ethanediyl]]bis-carbamic acid, bis(phenylmethyl)ester was added 3 ml of hydrogen bromide saturated glacial acetic acid. This mixture was stirred overnight, quenched in 400 ml of ether and the solid washed with ether and dried, giving 45 mg of the desired product, mp 188° C. (dec.).

EXAMPLE 93

N,N'-[(9,10-Dihydro-5,8-dihydroxy-9,10-dioxo-1,4-anthracencdiyl)bis(imino-2,1-ethanediyl)][L-alanyl-L-seryl-carbobenzyloxy-L-argininamide]dihydrobromide A 2.0 g portion of carbobenzyloxy-L-arginine hydrobromide and 796 mg of hydroxybenzotriazole monohydrate were dissolved in 20 ml of dimethylformamide and then chilled to −10° C. for 15 minutes. A 1.071 g portion of dicyclohexylcarbodiimide was dissolved in 10 ml of dimethylformamide and added to the above solution. This mixture was stirred for one hour at 0° C., then for one hour at room temperature and then filtered. The filtrate was added to a solution of 1.80 g of N,N'-[(9,10-dihydro-5,8-dihydroxy-9,10-dioxo-1,4-anthracenediyl)bis(imino-2,1-ethanediyl)]-bis[L-seryl-L-alaninamide]bis(trifluoroacetate) and 1.4 ml of diisopropyl ethylamine in dimethylformamide. This mixture was stirred for 5 hours, then evaporated and the residue triturated with ethyl acetate, giving 3.94 g of crude product. Trituration with water and subsequent drying gave a purer product of Rf 0.8 in a tetrahydrofuran:acetic acid:water 13:2:1 tlc system, mp 150° C. (dec.).

EXAMPLE 94

N,N'-[(9,10-Dihydro-5,8-dihydroxy-9,10-dioxo-1,4-anthracenediyl)bis(imino-2,1-ethanediyl)]bis[L-arginyl-L-seryl-L-alaninamide], tetrahydrobromide A 400 mg portion of the compound of Example 93 was added to 40 ml of water, stirred for 15 minutes and the solid recovered (230 mg). A 200 mg portion was added to 14 ml of hydrogen bromide saturated glacial acetic acid, stirred for one hour, quenched in ether and the solid collected and dried, giving 165 mg of the desired product, Rf 0.4 (system A).

EXAMPLE 95

[S-(R*,R*)][(9,10-Dihydro-5,8-dihydroxy-9,10-dioxo-1,4-anthracenediyl)bis[imino-2,1-ethanediylimino[1-[3-[[imino[[(phenylmethoxy)carbonyl]amino]methyl][(-phenylmethoxy)carbonyl]propyl]-2-oxo-2,1-ethanediyl]]]carbamic acid, bis(phenylmethyl)ester A 1.73 g portion of tris(carbobenzyloxy-L-arginine) was mixed with 40 ml of ethyl acetate. A 0.36 ml portion of N-methylmorpholine was added followed by 50 ml of tetrahydrofuran. This mixture was chilled for 15 minutes at −5° C., then 0.40 ml of isobutylchloroformate was added. After 3 minutes, 345 mg of hydroxysuccinimide was added and the mixture was stirred at room temperature overnight. The mixture was filtered and the filtrate diluted with twice its volume of heptane and chilled. The solid was collected, dried, then recrystallized from ethyl acetate-petroleum ether, giving 1.456 g of the hydroxysuccinimide ester of tris(carbobenzyloxy-L-arginine).

A 1 g portion of this ester was dissolved in 50 ml of dimethylformamide and added to a mixture of 239 mg of 1,4-bis[(2-aminoethyl)amino]-5,8-dihydroxyanthraquinone in 175 ml of dimethylformamide. The mixture was stirred overnight, evaporated to dryness, triturated with water, adjusted to pH 1.8 with 1N hydrochloric acid, and the solid collected and dried, giving 1.058 g of the desired product, mp 212° C. (dec.).

EXAMPLE 96

N,N'-[(9,10-Dihydro-5,8-dihydroxy-9,10-dioxo-1,4-anthradenediyl)bis(imino-2,1-ethanediyl)]bis[N-[(phenylmethoxy)carbonyl]-L-seryl-L-alanyl-L-leucyl-L-leucin-amide]

A solution of 1.04 g of carbobenzyloxy-L-seryl-L-alanyl-L-leucyl-L-leucine and 230 mg of hydroxysuccinimide in 25 ml of dimethylformamide was cooled in an ice bath and 412 mg of dicyclohexylcarbodiimide added. The mixture was stirred at 5° C. for 16 hours and then filtered. A 320 mg portion of 1,4-bis[(2-aminoethyl)amino]-5,8-dihydroxyanthraquinone, was added to the filtrate, then stirred at room temperature for 42 hours and centrifuged. The supernatant was decanted and the residue slurried with ether, giving 602 mg of the desired product, mp 193° C.

EXAMPLE 97

N,N'-[(9,10-Dihydro-5,8-dihydroxy-9,10-dioxo-1,4-anthracenediyl)-bis(imino-2,1-ethanediyl)]bis-[L-seryl-L-alanyl-L-leucyl-L-leucin- amide], dihydrobromide A 500 mg portion of N,N'-[(9,10-dihydro-5,8-dihydroxy-9,10-dioxo-1,4-anthracenediyl)bis (imino-2,1-ethanediyl)]-bis[N-[(phenylmethoxy)carbonyl]-L-seryl-L-alanyl-L-leucyl-L-leucinamide was dissolved in 15 ml of hydrogen bromide saturated glacial acetic acid, stirred for 4 hours and then diluted with 100 ml of ether. The solid was collected, washed with ether and dried in vacuo, giving 320 mg of the desired compound, HPLC 55:36:45:45=237 seconds.

EXAMPLE 98

N,N'-[(9,10-Dihydro-5,8-dihydroxy-9,10-dioxo-1,4-anthracenediyl)-bis(imino-2,1-ethanediyl)]bis-[N-[(9H-fluoren-9-ylmethoxy)carbonyl]-L-α-aspartyl-L-seryl-L-alanyl-L-leucyl-L-leucinamide], bis(1,1-dimethylethyl)ester Reaction of 246.9 mg of fluorenylmethyloxycarbonyl aspartic acid, 8-tertiary butyl ester, 72.8 mg of N-methylmorpholine, 98 mg of isobutylchloroformate, and 82.9 mg of N-hydroxysuccinimide in 10 ml of ethyl acetate, as described in Example 38, gave the corresponding hydroxysuccinimide ester.

This ester in 4.5 ml of dimethylformamide was added to N,N'-[(9,10-dihydro-5,8-dihydroxy-9,10-dioxo-1,4-anthracenediyl)bis(imino-2,1-ethanediyl)]bis[L-seryl-L-alanyl-L-leucyl-L-leucinamide], dihydrobromide and 0.153 ml of diisopropylethylamine in 4.5 ml of dimethylformamide. This mixture was stirred for 16 hours, then filtered and the filtrate concentrated in vacuo. The residue was triturated with ether and the solid collected, washed with ether and dried in vacuo, giving 228 mg of the desired product, mp 188° C.

EXAMPLE 99

N,N'-[(9,10-Dihydro-5,8-dihydroxy-9,10-dioxo-1,4-anthracenediyl)-bis(imino-2,1-ethanediyl)]bis)[L-α-aspartyl-L-seryl-L-alanyl-L-leucyl-L-leucinamide], bis(1,1-dimethylethyl)ester To a 200 mg portion of N,N'-[(9,10-dihydro-5,8-dihydroxy-9,10-dioxo-1,4-anthracenediyl)bis(imino2,1-ethanediyl)]bis[N-[(9H-fluoren-9-ylmethoxy)carbonyl]-L-α-aspartyl-L-seryl-L-ala nyl-L-leucyl-L-leucinamide]bis-(1,1-dimethylethyl)ester in 10 ml of dimethylformamide was added 10 ml of dimethylformamide saturated with dimethylamine. After standing 30 minutes the solution was concentrated in vacuo and the residue dried in vacuo, giving 152 mg of the desired compound, mp 205° C.

EXAMPLE 100

N,N'-[(9,10-Dihydro-5,8-dihydroxy-9,10-dioxo-1,4-anthracenediyl)bis(imino-2,1-ethanediyl)]-[N-[(9H-fluoren-9-ylmethoxy)carbonyl]-L-α-aspartyl-L-alaninamide], bis(1,1-dimethylethyl)ester To a solution of fluorenylmethyloxycarbonyl aspartic acid, 8-tertiary butyl ester, hydroxysuccinimide ester (prepared from 1.85 g of fluoroenylmethyloxycarbonyl aspartic acid, β-tertiaryl butyl ester, 564 mg of N methylmorpholine, 738 mg of isobutylchloroformate and hydroxysuccinimide) in 50 ml of dimethylformamide, was added 1.03 g of N,N'-[(9,10-dihydro-5,8-dihydroxy-9,10-dioxo-1,4-anthracenediyl)bis(imino-2,1-ethanediyl)]bis[L-alanine]di-hydrochloride and 1.16 g of diisopropylethylamine. The reaction mixture was stirred 72 hours, then filtered, the filtrate concentrated to a small volume in vacuo, then diluted with 150 ml of ether. The solid was collected, dried in vacuo, slurried in 50 ml of water and the solid collected and dried in vacuo, giving 1.2 g of the desired product, mp 190° C.

EXAMPLE 101

N,N'[(9,10-Dihydro-5,8-1,4-anthracenediyl)bis(imino-2,1-ethanediyl)]bis[L-α-aspartyl-L-alaninamide], bis(1,1-dimethylethyl)ester To 1.1 g of N,N'-[(9,10-dihydro-5,8-dihydroxy-9,10-dioxo-1,4-anthracenediyl)bis(imino-2,1-ethanediyl)]-bis[N-[(9H-fluoren-9-ylmethoxy)carbonyl]-L-α-aspartyl-L-alanamide]bis(1,1-dimethylethyl)ester in 25 ml of dimethylformamide was added 25 ml of dimethylformamide saturated with dimethylamine. After standing 30 minutes the mixture was concentrated to a small volume and then diluted with 100 ml of ether. The solid was collected, washed with ether and dried in vacuo, giving 908 mg of the desired product, mp 200° C.

EXAMPLE 102

N,N'-[(9,10-Dihydro-5,8-dihydroxy-9,10-dioxo-1,4-anthracenediyl)bis(imino-2,1-ethanediyl)]-[N-[(9H-fluoren-9-ylmethoxy)carbonyl]-glycyl-glycyl-L-α-aspartyl-L-alaninamide], bis(1,1-dimethylethyl)ester To a solution of fluorenylmethyloxycarbonyl glycyl glycine hydroxysuccinimide ester (prepared from 433 mg of fluoroenylmethyloxycarbonyl glycyl glycine and 159 mg of hydroxysuccinimide and dicyclohexylcarbodiimide) in 75 ml of dimethylformamide was added 598.6 mg of N,N'-(9,10-dihydro-5,8-dihydroxy-9,10-dioxo-1,4-anthracenediyl)-bis(imino-2,1-ethanediyl)-]bis[L-α-aspartyl-L-alanine]-bis(1,1-dimethyethyl)este r and 248 mg of diisopropylethylamine. The mixture was stirred overnight, then filtered and the filtrate concentrated to a small volume. This was diluted with ether, the solid collected, washed with ether and dried in vacuo, giving 915 mg of the desired product, mp 175° C.

EXAMPLE 103

N,N'-[(9,10-Dihydro-5,8-dihydroxy-9,10-dioxo-1,4-anthracenediyl)bis(imino-2,1-ethanediyl)]-bis[glycylglycyl-L-α-aspartyl-L-alaninamide], bis(1,1-dimethylethYl)ester To 800 mg of N,N'-[(9,10-dihydroxy-9,10-dioxo-1,4-anthracenediyl)bis(imino-2,1-ethanediyl)]-bis[N-[(9H-fluoren-9-ylmethoxy)carbonyl]glycyglycyl-L-α-aspartyl-L-alaninam ide], bis(1,1-dimethylethyl)ester in ≅ml of dimethylformamide was added 25 ml of dimethylformamide saturated with dimethylamine. After 30 minutes the mixture was concentrated to a small volume, then diluted with 150 ml of ether, the solid collected, washed with ether and dried in vacuo, giving 614 mg of the desired product, mp 180° C.

EXAMPLE 104

N,N'-[(9,10-Dihydro-5,8-dihydroxy-9,10-dioxo-(1,4-anthracenediyl)bis(imino-2,1-ethanediyl)]bis[glycylglycyl-L-α-aspartyl-L-alaninamide]

A 60 mg portion of N,N'-[(9,10-dihydro-5,8-dioxo-1,4-anthracenediyl)bis(imino-2,1-ethanediyl)]bis[-glycylglycyl-L-α-aspartyl-L-alaninamide], bis(1,1-dimethylethyl)ester was slurried in 0.8 ml of anisole and cooled in an ice bath. A 1.6 ml portion of trifluoroacetic acid was added, the solution was stirred in the ice bath for 15 minutes, then at room temperature for 1 hour and diluted with 50 ml of ether. The solid was collected, washed with ether and dried in vacuo, giving mg of the desired product, mp 150°°C.

EXAMPLE 105

N,N'-[(9,10-Dihydro-5,8-dihydroxy-9,10-dioxo-1,4-anthracenediyl)bis(imino-2,1-ethanediyl)]-bis[N-[(9H-fluoren-9-ylmethoxy)carbonyl]-L-α-aspartyl-glycyl-L-alanyl-L-prolinamide], bis(1,1-dimethylethyl)ester A solution of fluroenylmethyloxycarbonyl-L-α-aspartyl tertiary butyl ester-glycyl-L-alanyl-L-proline and hydroxysuccinimide in 30 ml of dimethylformamide was cooled in an ice bath and dicyclohexylcarbodiimide added. After 16 hours at 5° C. the reaction mixture was filtered and 142 mg of 1,4-bis[(2-aminoethyl)amino]-5,8-dihydroxyanthraquinone, added. After 60 hours at room temperature the mixture was centrifuged, the supernatant filtered and the filtrate concentrated in vacuo. The residue was slurried with ether, the solid collected, washed with ether and dried in vacuo, giving 763 mg of the desired product, mp 160° C.

EXAMPLE 106

N,N'-[(9,10-Dihydro-5,8-dihydroxy-9,10-dioxo-1,4-anthracenediyl)bis(imino-2,1-ethanediyl)]-bis[L-α-aspartyl-glycyl-L-alanyl-L-prolinamide], bis(1,1-dimethylethyl)ester To a solution of 700 mg of N,N'-[(9,10-dihydro-5,8-dihydroxy-9,10-dioxo-1,4-anthracendiyl)bis(imino-2,1-ethandiyl)]bis[N-[(9H-fluoren-9-ylmethoxy)carbonyl]-L-α-aspartyl-glycyl-L-alanyl-L-p rolinamide], bis(1,1-dimethylethyl)ester in 25 ml of dimethylformamide was added 25 ml of dimethylformamide saturated with dimethylamine. After 1 hour the mixture was concentrated in vacuo, the residue slurried with ether, the solid collected, washed with ether and dried in vacuo, giving 501 mg of the desired compound, mp 145° C.

EXAMPLE 107

N,N'-[(9,10-Dihydro-5,8-dihydroxy-9,10-dioxo-1,4-anthracenediyl)bis(imino-2,1-ethanediyl)]-bis[L-α-aspartyl-L-alaninamide], bis(trifluoroacetate A 60 mg portion of N,N'-[(9,10-dihydro-5,8-dihydroxy-9,10-dioxo-1,4-anthracenediyl)bis(imino-2,1-ethanediyl)]bis[L-α-aspartyl-L-alaninamide], bis(1,1-dimethylethyl)ester was slurried in 0.8 ml of anisole and cooled in an ice bath. A 1.6 ml portion of trifluoroacetic acid was added and the mixture was stirred at 0° C. for 15 minutes then at room temperature for 1 hour. The mixture was then diluted with 50 ml of ether, the solid collected, washed with ether and dried in vacuo, giving 46.5 mg of the desired product, mp 180° C.

EXAMPLE 108

N,N'-[(9,10-Dihydro-5,8-dihydroxy-9,10-dioxo-1,4-anthracenediyl)bis(imino-2,1-ethanediyl)]-bis[(9H-fluoren-9-ylmethoxy)carbonyl]-L-leucyl-L-alanyl-L-leucyl-L-methioninamide]

To solution of fluoroenylmethyloxycarbonyl-L-leucyl-L-alanyl-L-leucine, hydroxysuccinimide ester, (prepared from 1.083 g of fluoroenylmethyloxycarbonyl-L-leucyl-L-alanyl-L-leucine, 0.255 g of hydroxysuccinimide and 0.457 g of dicyclohexylcarbodiimide) in dimethylformamide was added 0.728 g of N,N'-[9,10-dihydro-5,8-dihydroxy-9,10-dioxo-1,4-anthracenediyl)-bis(imino-2,1-ethanediyl)]bis(methionine)dihydrochloride and 0.28 ml of triethylamine. This mixture was stirred overnight, then centrifuged. The supernatant was concentrated to a small volume in vacuo, diluted with ether, the solid collected and dried in vacuo, giving 576 mg of the desired product, mp 240° C.

EXAMPLE 109

N,N'-[(9,10-Dihydro-5,8-dihydroxy-9,10-dioxo-1,4-anthracenediyl)bis(imino-2,1-ethanediyl)]-bis[L-leucyl-L-alanyl-L-leucyl-L-methioninamide]

To a solution of 550 mg of N,N'-[(9,10-dihydro-5,8-dihydroxy-9,10-dioxo-1,4-anthracenediyl)bis(imino-2,1-ethanediyl)]bis[N-[(9H-fluoren-9-ylmethoxy)carbonyl]-L-leucyl-L-alanyl-L-leuc yl-L-methioninamide]in 10 ml of dimethylformamide was added 15 ml of dimethylformamide saturated with dimethylamine. After 30 minutes the mixture was concentrated in vacuo to a small volume, diluted with 50 ml of ether, the solid collected and dried in vacuo, giving 456 mg of the desired product, mp 210° C.

EXAMPLE 110

N,N'-[(9,10-Dihydro-5,8-dihydroxy-9,10-dioxo-1,4-anthracenediyl)bis(imino-2,1-ethanediyl)]-bis[N-[(9H-fluoren-9-ylmethoxy)carbonyl]-L-α-artyl-glycyl-L-alanyl-L-prolyl-L-methioninamide 9 , bis(1,1-dimethylethyl)ester To a solution of fluorenylmethyloxycarbonyl-L-α-aspartyl tertiary butyl ester-glycyl-L-alanyl-L-proline, hydroxysuccinimide ester (prepared from 690 mg of fluorenylmethyloxycarbonyl-L-α-aspartyl tertiaryl butyl ester-glycyl-L-alanyl-L- proline, 127 mg of hydroxysuccinimide and 227 mg of dicyclohexylcarbodiimide) in 15 ml of dimethylformamide was added 346 mg of N,N'-[(9,10-dihydro-5,8-dihydroxy-9,10-dioxo-1,4-anthracenediyl)bis(imino-2,1-ethanediyl)]bis(methionine), dihydrochloride and 0.28 ml of triethylamine. After 16 hours the reaction mixture was concentrated to a small volume in vacuo, diluted with ether, the solid collected and dried in vacuo, giving 1.16 g of the desired product, mp 155° C.

EXAMPLE 111

N,N'-[(9,10 -Dihydro-5,8-dihydroxy-9,10-dioxo-1,4-anthracenedivl)bis(imino-2,1-ethanediyl)]-bis[L-α-aspartyl-glycyl-L-alanyl-L-prolyl-L-methioninamide], bis(1,1-dimethylethyl)ester Dimethylamine was passed into a cooled solution of 500 mg N,N'-[(9,10-dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-glycyl-L-alanyl-L-prolyl-L- methioninamide], bis(1,1-dimethylethyl)ester in 20 ml of dimethylformamide for 4 minutes. After 30 minutes at room temperature the solution was concentrated to a small volume in vacuo, then diluted with ether, the solid collected and dried in vacuo, giving 373 mg of the desired compound, mp 165° C.

EXAMPLE 112

N,N'-[(9,10-Dihydro-5,8-dihydroxy-9,10-dioxo-1,4-anthracenediyl)bis(imino-2,1-ethanediyl)]-bis[L-α-aspartyl-glycyl-L-alanyl-L-prolyl- L-methioninamide]

A 73 mg portion of N,N'-[(9,10-dihydro-5,8-dihydroxy-9,10-dioxo-1,4-anthracenediyl)bis(imino-2,1-ethanediyl)]bis[L-α-aspartyl-glycyl-L-alanyl-L-prolyl-L-methioninamide], bis(1,1-dimethylethyl)ester was slurried in 0.75 ml of anisole cooled in an ice bath. A 1.5 ml portion of trifluoroacetic acid was added, the solution maintained at 5° C. for 15 minutes, then at room temperature for 1.5 hours. The mixture was diluted with ether, the solid collected and dried in vacuo, giving 52 mg of the desired compound, mp 180° C.

EXAMPLE 113

N,N'-[(9,10-Dihydro-5,8-dihydroxy-9,10-dioxo-1,4-anthracenediyl)bis(imino-2,1-ethanediyl)]-bis[N-[(phenylmethoxy)carbonyl]-L-phenyl-alanyl-L-leucinamide]

A mixture of 2.73 g of carbobenzyloxy-L-phenylalanyl hydroxysuccinimide ester, 2.6 ml of triethylamine and 2.43 g of [S-(R*,R*)]-N,N'-[(9,10-dihydro-5,8-dihydroxy-9,10-dioxo-1,4-anthracenediyl)bis(imino-2,1-ethanediyl)]-bis[2-amino-4-methylpentanamide]ditrifluoroacetate in 100 ml of dimethylformamide was reacted as described in Example 51, giving 3.215 g of the desired product, mp 240° C. (dec.).

EXAMPLE 114

N,N'-[(9,10-Dihydro-5,8-dihydroxy-9,10-dioxo-1,4-anthracenediyl)bis(imino-2,1-ethanediyl)]-bis[L-phenylalanyl-L-leucinamide], dihydrobromide A 2.75 g portion of N,N'-[(9,10-dihydro-5,8-dihydroxy-9,10-dioxo-1,4-anthracenediyl)bis(imino-2,1-ethanediyl)]bis[N-[(phenylmethoxy)carbonyl]-L-phenylalanyl-L-leucinamide] was reacted by a modification of the procedure of Example 31, by being dissolved in 75 ml of glacial acetic acid previously saturated for 5 minutes with anhydrous hydrogen bromide. The mixture was reacted for 2.5 hours, then more hydrogen bromide was bubbled into the solution for 15 minutes and after another 2 hours the solid was collected, giving 2.7 g of the desired product, mp 180° C. (dec.).

EXAMPLE 115

N,N'-[(9,10-Dihydro-5,8-dihydroxy-9,10-dioxo-1,4-anthracenediyl)bis(imino-2,1-ethanediyl)]-bis[N-[(phenylmethoxy)carbonyl]-L-phenyl-alanyl-L-phenylalanyl-L-leucinamide]

Reaction of 1.822 g of carbobenzyloxy-L-phenylalanyl hydroxysuccinimide ester with 2.076 g of N,N'-[(9,10-dihydro-5,8-dihydroxy-9,10-dioxo-1,4-anthracenediyl)bis(imino-2,1-ethanediyl)]bis[L-phenylalanyl-L-leucinamide], dihydrobromide and 1.73 ml of triethylamine, in the manner of Example 51, gave 2.3 g of the desired product, mp 250° C. (dec.).

EXAMPLE 116

[S-(R*,R*,R*,R*)]-4,4'-[(9,10-Dihyro-5,8-dihydroxy-9,10-dioxo-1,4-anthracenediyl)-bis(imino-2,1-ethanediylimino)]bis[3-[[2-[[(9H-fluoren-9-ylmethoxy)-carbonyl]amino]- b 4-methyl-1-oxopentyl]amino]-4-oxobutanoic acid], bis(1,1-dimethylethyl)ester Reaction of 1.09 of fluorenylmethyloxylcarbonyl-L-leucine, 0.373 ml of N-methylmorpholine, 0.44 ml of isobutoxycarbonyl chloride and 0.391 g of N-hydroxysuccinimide in 50 ml of ethyl acetate, following the method of Example 38, gave the corresponding hydroxysuccinimide ester. Reaction of this ester with 0.7 g of [S-(R*,R*)]-4,4'-[(9,10-dihydro-5,8-dihydroxy-9,10-dioxo-1,4-anthracenediyl)bis(imino-2,1-ethanediylimino)]bis[3-amino-4-oxobutanoic acid], bis(1,1-dimethylethyl)ester whose preparation is described in Example 39) in 50 ml of dimethylformamide, following the general procedure of Example 51, gave 0.89 g of the desired product, mp 162° C. (dec.).

EXAMPLE 117

N,N'-[(9,10-Dihydro-5,8-dihydroxy-9,10-dioxo-1,4-anthracenediyl)bis(imino-2,1-ethanediyl)]-bis[L-phenylalanyl-L-phenylalanyl-L-leucinamide], dihydrobromide Reaction of 2 g of [S-(R*,R*,R*,R*)]-4,4'-[(9,10-dioxo-1,4-anthracenediyl)bis(imino-2,1-ethanediylimino)]-bis[3-[[2-[[(9H-fluoren-9-ylmethoxy)carbonyl]amino]-4-methyl-1-oxopentyl]amino]-4-oxobutanoic acid], bis(1,1-dimethylethyl)ester with 60 ml of hydrogen bromide-saturated glacial acetic acid for 2 hours, following the general method of Example 31, gave 1.65 g of the desired product, mp 197°°C.

EXAMPLE 118

[S-(R*,R*,R*,R*)]-4,4'-[(9,10-Dihydro-5,8-dihydroxy-9,10-dioxo-1,4-anthracenediyl)-bis(imino-2,1-ethanediylimino)]bis[3-[(2-amino-4-methyl-1-oxopentyl)amino]-4-oxobutan oic acid], bis(1,1-dimethylethyl)ester Following the procedure of Example 39, 0.75 g of S-(R*,R*,R*,R*)]-4,4'-[(9,10-dihydro-5,8-dihydroxy-9,10-dioxo-1,4-anthracenediyl)bis(imino-2,1-ethanediylimino)]-bis[3-[[2-[[(9H-fluoren-9-ylmethoxy)carbonyl]amino]-4-methyl-1-oxopentyl]amino]-4-oxobutanoic acid], bis(1,1-dimethylethyl)ester was reacted with dimethylamine in dimethylformamide for 22 minutes, giving 0.33 g of the desired product, mp 130° C. (dec.).

EXAMPLE 119

N,N'[(9,10-Dihydro-5,8-dihydroxy-9,10-dioxo-1,4-anthracenediyl)bis(imino-2,1-ethanediyl)]-bis[N-[(1,1-dimethylethoxy)carbonyl]-glycyl-L-phenylalanyl-L-phenylalanyl-L-leucinamide]

Following the method of Example 51, 1.34 g of N,N'-[(9,10-dihydro-5,8-dihydroxy-9,10-dioxo-1,4-anthracenediyl)bis(imino-2,1-ethanediyl)]bis[L-phenylalanyl-L-phenyl-alanyl-L-leucinamide], dihydrobromide, 0.68 g of t-butyloxycarbonyl-glycyl hydroxysuccinimide ester and 0.86 ml of triethylamine in 100 ml of dimethylformamide were reacted, giving 1.16 g of the desired product, mp >260°0 C.

EXAMPLE 120

N,N'-[(9,10-Dihydro-5,8-dihydroxy-9,10-dioxo-1,4-anthracenediyl)bis(imino-2,1-ethanediyl)]-bis[glycyl-L-phenylalanyl-L-phenylalanyl-L-leucinamide], bis(trifluoroacetate)

Using a slight modification of the procedure of Example 26, 0.66 g of N,N'-[(9,10-dihydro-5,8-dihydroxy-9,10-dioxo-1,4-anthracenediyl)bis(imino-2,1-ethanediyl)] bis[N-[(1,1-dimethylethoxy)carbonyl]glycyl-L-phenylalanyl-L-phenylalanyl-L-leucinamide] in 6.6 ml of anisole and 13 ml of trifluoroacetic acid was reacted for 5 minutes at 5° C. and then 3 hours at room temperature, giving 0.58 g of the desired product, mp 255° C.

EXAMPLE 121

N,N'-[(9,10-Dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-leucyl-L-alanyl-L-leucinamide], bis(1,1-dimethyethyl)ester A 1.21 g portion of fluorenylmethyloxycarbonyl aspartic acid, β-tertiary butyl ester was converted to the corresponding hydroxysuccinimide ester, according to the procedure of Example 38. This ester was reacted with N,N'-[(9,10-dihydro-5,8-dihydroxy-9,10-dioxo-1,4-anthracenediyl)bis(imino-2,1-ethanediyl)]bis[L-leucyl-L-alanyl-L-leucinamide]dihydrobromide in 75 ml of dimethylformamide, by the procedure of Example 51 in the presence of 0.73 ml of diisopropylethylamine, giving 1.64 g of the desired product, mp 240° C. (dec.).

EXAMPLE 122

N,N'-[(9,10-Dihydro-5,8-dihydroxy-9,10-dioxo-1,4-anthracenediyl)bis(imino-2,1-ethanediyl)]bis[L-α-aspartyl-L-leucyl-L-alanyl-L-leucinamide], bis(1,1-dimethylethyl)ester A solution of 1.3 g of N,N'-[(9,10-dihydro-5,8-dihydroxy-9,10-dioxo-1,4-anthracenediyl)bis(imino-2,1-ethanediyl)]bis[N[(9H-fluoren-9-ylmethoxy)carbonyl]-L-α-aspartyl-L-leucyl-L-alanyl-L-leucinamide], bis(1,1-dimethylethyl)ester in 50 ml of dimethylformamide was treated for 10 minutes with dimethylamine, as described in Example 39, giving 0.88 g of the desired product, mp 251° C. (dec.).

EXAMPLE 123

[S-(R*,R*)]-[(9,10-Dihydro-5,8-dihydroxy-9,10-dioxo-1,4-anthracenediyl)bis(imino-2,1-ethanediyl[(2-hydroxyethyl)imino][1-[2-(methylthio)ethyl]-2-oxo-2,1-ethanediyl]]]bis carbamic acid, bis(9H-fluoren-9-ylmethyl)ester Using the method of Example 2, 2.2 g of fluorenylmethyloxycarbonyl-L-methionine was converted to its symmetrical anhydride with 0.62 g of dicyclohexycarbodiimide in 14 ml of dimethylformamide, and this was reacted with 0.444 g of 1,4-dihydroxy-5,8-bis[[2-(2-hydroxyethylamino)ethyl]- amino]anthraquinone in 20 ml of dimethylformamide. Workup as described in Example 2 gave 1.39 g of the desired product, mp 112° C. (dec.).

EXAMPLE 124

[S-(R*,R*)]-[(9,10-Dihydro-5,8-dihydroxy-9,10-dioxo-1,4-anthracenediyl)bis[imino-2,1-ethanediyl[(2-hydroxyethyl)imino](1-oxo-1,2,6-hexanetriyl)]]tetrakis carbamic acid, tetrakis(phenylmethyl)ester As described in Example 2, 2.5 g of dicarbobenzyloxycarbonyl-L-lysine was converted to the symmetrical anhydride with 0.62 g of dicyclohexylcarbodiimide in 5 ml of dimethylformamide, and this was reacted with 0.444 g of 1,4-dihydroxy-5,8-bis[[2-(2-hydroxyethylamino)ethyl]amino]anthraquinone in 20 ml of dimethylformamide. Workup as described in Example 2 gave 1.56 g of the desired product, mp 136° C. (dec.).

EXAMPLE 125

[S-(R,*R*)]-N,N'-[(9,10-Dihydro-5,8-dihydroxy-9,10-dioxo-1,4-anthracenediyl)bis(imino-2,1-ethanediyl)-]bis[2,6-diamino-N-(2-hydroxyethyl)hexanamide], tetrakis(trifluoroacetate)

Treatment of 1 g of [S-(R*,R*)]-[(9,10-dihydro-5,8-dihydroxy-9,10-dioxo-1,4-anthracenediyl)bis[imino-2,1-ethanediyl[(2-hydroxyethyl)imino](1-oxo-1,2,6-hexanetriyl)]]-tetrakis carbamic acid, tetrakis(phenylmethyl)ester overnight with 25 ml of hydrogen bromide saturated trifluoroacetic acid, followed by isolation by quenching the reaction in 250 ml of ether and retreatment with hydrogen bromide saturated trifluoroacetic acid overnight, gave 0.56 g of the desired product, mp 158° C. (dec.).

EXAMPLE 126

[S-(R*,R*)]-[(9,10-Dihydro-5,8-dihydroxy-9,10-dioxo-1,4-anthracenediyl)bis[imino-2,1-ethanediyl[(2-hydroxyethyl)imino][1-[2-(methylthio)ethyl]-2-oxo-2,1-ethanediyl]]]bis carbamic acid, bis(phenylmethyl)ester Following the procedure of Example 2, 1.7 g of carbobenzyloxycarbonyl-L-methionine was converted to the symmetrical anhydride with 0.62 g of dicyclohexylcarbodiimide in 20 ml of dimethylformamide. This ester was reacted with 0.444 g of 1,4-dihydro-5,8-bis[[2-(2-hydroxyethylamino)ethyl]amino]anthraquinone in 20 ml of dimethylformamide overnight. The reaction mixture was evaporated, giving the desired product as a gum [Rf 0.75 in the TLC system chloroform:methanol:ammonium hydroxide (85:15:3)].

EXAMPLE 127

[S-(R*,R*)]-5,5'-[(9,10-Dihydro-5,8-dihydroxy-9,10-dioxo-1,4-anthracenediyl)bis[imino-2,1-ethanediyl[(2-hyroxyethyl)imino]]bis[4-[[(1,1-dimethylethoxy)carbonyl]amino]-5-oxopentanoic acid]], bis(1,1-dimethylethyl)ester Following the procedure of Example 2, 1.82 g of t-butoxycarbonyl-L-glutamic acid, γ-O-butyl ester was converted to its symmetrical anhydride with 0.62 g of dicyclohexylcarbodiimide in 18 ml of dimethylformamide. This compound was reacted with 0.444 g of 1,4-dihydroxy-5,8-bis[[2-(2-hydroxyethylamino)ethyl]amino]anthraquinone in 20 ml of dimethylformamide. The solvent was evaporated, the residue dissolved in chloroform and precipitated with petroleum ether, giving 0.97 g of the desired product, mp 100° C. (dec.).

EXAMPLE 128

[S-(R*,R*)]-5,5'-[(9,10-Dihydro-5,8-dihydroxy-9,10-dioxo-1,4-anthracenediyl)bis[imino-2,1-ethanediyl[(2-hydroxyethyl)imino]]bis[4-amino-5-oxopentanoic acid]], bis(trifluoroacetate)

Reaction of 0.30 g of [S-(R*,R*)]-5,5'-[(9,10-dihydro-5,8-dihydroxy-9,10-dioxo-1,4-anthracenediyl)bis[imino-2,1-ethanediyl[(2-hydroxyethyl)imino]]bis[4-[[(1,1-dimethylethoxy)carbonyl]amino]-5-oxopentanoic acid]], bis(1,1-dimethylethyl)ester with 3 ml of anisole and 6 ml of trifluoroacetic acid, as described in Example 27, gave 0.22 g of the desired product mp 147° C. (dec.).

EXAMPLE 129

[(9,10-Dihydro-5,8-dihydroxy-9,10-dioxo-1,4-anthracenediyl)bis[imino-2,1-ethanediyl-[(2-hydroxyethyl)imino](2-oxo-2,1-ethanediyl)]]bis-carbamic acid, bis (9H-fluoren-9-ylmethyl)ester Following the procedure of Example 2, 1.78 g of fluorenylmethyloxycarbonylglycine was transformed into its symmetrical anhydride with 0.62 g dicyclohexylcarbodiimide in 13 ml of dimethylformamide. This compound was added to 0.444 g of 1,4-dihydro-5,8-bis[[2-(2-hydroxyethylamino)ethyl]amino]anthraquinone in 20 ml of dimethylformamide. Evaporation of the solvent and addition of 250 ml of ethyl acetate followed by filtration gave a solution which was treated as described in Example 2, giving 0.95 g of the desired product, mp 110° C. (dec.).

EXAMPLE 130

N,N'-[(9,10-Dihydro-5,8-dihydroxy-9,10-dioxo-1,4-anthracenediyl)bis(imino-2,1-ethanediyl)]bis[2-amino-N-(2-hydroxyethyl)acetamide]

Following the procedure of Example 39, 0.3 g of [(9,10-dihydro-5,8-dihydroxy-9,10-dioxo-1,4-anthracenediyl)bis[imino-2,1-ethanediyl[(2-hydroxyethyl)imino](2-oxo-2,1-ethanediyl)]]bis-carbamic acid, bis(9H-fluoren-9-ylmethyl)ester in 5 ml of dimethylformamide was treated with dimethylamine in 6 ml of dimethylformamide, giving 0.11 g of the desired product, mp 162° C. (dec.).

EXAMPLE 131

[S-(R*,R*)]-N,N'-[(9,10-Dihydro-5,8-dihydroxy-9,10-dioxo-1,4-anthracenediyl)bis(imino-2,1-ethanediyl)-]bis[2-amino-N-(2-hydroxyethyl)-4-(methylthio)butanamide]

Following the procedure of Example 39, 0.3 g of [S-(R*,R*)]-[(9,10-dihydro-5,8-dihydroxy-9,10-dioxo-1,4-anthracenediyl)bis[imino-2,1-ethanediyl[(2-hydroxyethyl)imino][1-[2-(methylthio)ethyl]-2-oxo-2,1-ethanediyl]]]bis carbamic acid, bis(9H-fluoren-9-ylmethyl)ester in 5 ml of dimethylformamide was treated with dimethylamine in 6 ml of dimethylformamide, giving 79 mg of the desired product, mp 119° C. (dec.).

EXAMPLE 132

N,N'-[(9,10-Dihydro-5,8-dihydroxy-9,10-dioxo-1,4-anthracenediyl)bis(imino-2,1-ethanediyl)]bis[N-(9H-fluoren-9-ylmethoxy)carbonyl]glycyl-L-α-aspartyl-L-alanyl-L-leucinamide, bis(1,1-dimethylethyl)ester A solution of fluroenylmethyloxycarbonylglycine, hydroxysuccinimide ester was prepared by reaction of 0.3 g of fluorenylmethyloxycarbonylglycine, 0.13 g of N-hydroxysuccinimide and 0.23 g of dicyclohexylcarbodiimide in 5 ml of tetrahydrofuran for 1 hour at 5° C., then 18 hours at 10° C. Filtration of the dicyclohexyl urea precipitate and evaporation of the filtrate gave the hydroxysuccinimide ester. This ester was dissolved in dimethylformamide and reacted with 0.36 g of N,N'-[(-9,10-dihydro-5,8-dihydroxy-9,10-dioxo-1,4-anthracenediyl)bis(imino-2,1-ethanediyl)]bis[N-[(9H-fluoren-9-ylmethoxy)carbonyl]-L-α-aspartyl-L-α-alanyl-L-leucinamide]bis(1,1-dimethylethyl)ester by the procedure of Example 38, giving 0.4 g of the desired product, mp 225° C. (dec.).

EXAMPLE 133

N,N'-[(9,10-Dihydro-5,8-dihydroxy-9,10-dioxo-1,4-anthracenediyl)bis(imino-2,1-ethanediylimino-[1-[2-(1,1-dimethylethoxyl-2-oxoethyl-2,1-ethanediyl]]]bis[N-[(9H-fluoren-9-ylmethoxy)-carbonyl]-L-leucyl-L-alanyl-L-leucinamide]

A solution of fluorenylmethyloxycarbonyl-L-leucyl-L-alanyl-L-leucine, hydroxysuccinimide ester was prepared from 1.08 g of the corresponding acid and 2.2 mmole each of hydroxysuccinimide and dicyclohexylcarbodiimide in 15 ml of tetrahydrofuran as described in Example 132. Reaction with 0.48 g of [S-(R*,R*)]-4,4'-[(9,10-dihydro-5,8-dihydroxy-9,10-dioxo-1,4-anthracenediyl)bis(imino-2,1-ethanediylimino)bis[3-amino-4-oxobutanoic acid]bis(1,1-dimethylethyl)ester, following the procedure of Example 38 gave 1.47 g of the desired product in two crops, mp 200° C. (dec.).

EXAMPLE 134

N,N'-[(9,10-Dihydro-5,8-dihydroxy-9,10-dioxo-1,4-anthracenediyl)bis(imino-2,1-ethanediyl)]bis[N-[(9H-fluoren-9-ylmethoxy)carbonyl]glycylglycyl-L-α-aspartyl-L-alanyl-L-leucinamide]bis(1,1-dimethylethyl)ester A solution of fluorenylmethyloxycarbonyl-glycylglycine, hydroxysuccinimide ester was prepared from 0.52 g of fluorenylmethyloxycarbonyl-glycylglycine, 0.19 g of N-hydroxysuccinimide and 0.33 g of dicyclohexylcarbodiimide in 30 ml of tetrahydrofuran, as described in Example 132. This was reacted with 0.53 g of N,N'-[(9,10-dihydro-5,8-dihydroxy-9,10-dioxo-1,4-anthracenediyl)bis(imino-2,1-ethanediyl)]bis[N-(9H-fluoren-9-ylmethoxy)carbonyl]-L-α-aspartyl-L-alanyl-L-leucinamide]bis(1,1-dimethylethyl)ester, following the procedure of Example 38, giving 0.66 g of the desired product, mp 220° C. (dec.).

EXAMPLE 135

N,N'-[(9,10-Dihydro-5,8-dihydroxy-9,10-dioxo-1,4-anthracenediyl)bis(imino-2,1-ethanediylimino)]bis[[1-[2-(1,1-dimethylethoxy)-2-oxoethyl]-2-oxoethyl]-2-oxo-2,1-ethanedily]bis[L-leucyl-L-alanyl-L-leucinamide]

A solution of 0.4 g of N,N'-[(9,10-dihydro-5,8-dihydroxy-9,10-dioxo-1,4-anthrancenediyl)bis[imino-2,1-ethanediylimino-[1-[2-(1,1-dimethylethoxy)-2-oxoethyl]-2-oxo-2,1-ethanediyl]]]-bis[N-[(9H-fluoren-9-ylmethoxy)carbonyl]-L-leucyl-L-alanyl-L-leucinamide] was treated with dimethylamine in 4 ml of dimethylformamide, as described in Example 39, giving 0.26 g of the desired product, mp 205° C. (dec.).

EXAMPLE 136

N,N'-[(9,10-Dihydro-5,8-dihydroxy-9,10-dioxo-1,4-anthracenediyl)bis(imino-2,1-ethanediyl)]bis[glycylglycyl-L-α-aspartyl-L-alanyl-L-leucinamide], bis(1,1-dimethylethyl)ester A solution of 0.4 g of N,N'-[(9,10-dihydro-5,8-dihydroxy-9,10-dioxo-1,4-anthracenediyl)bis(imino-2,1-ethanediyl)]bis[N-[(9H-fluoren-9-ylmethoxy)carbonyl]-glycylglycyl-L-α-aspartyl-L-alanyl-L-leucinamide], bis(1,1-dimethylethyl) ester was treated with dimethylamine in 8 ml of dimethylformamide as described in Example 39, giving 0.3 g of the desired product, mp 228° C. (dec.).

EXAMPLE 137

N,N'-[(9,10-Dihydro-5,8-dihydroxy-9,10-dioxo-1,4-anthracenediyl)bis(imino-2,1-ethanediyl)]bis[glycyl-L-α-aspartyl-L-alanyl-L-leucinamide], bis(1,1-dimethylethyl)ester A solution of 0.3 g of N,N'-[(9,10-dihydro-5,8-dihydroxy-9,10-dioxo-1,4-anthracenediyl)bis(imino-2,1-ethanediyl)]bis[N-(9H-fluoren-9-ylmethoxy)carbonyl]-glycyl-L-α-aspartyl-L-alanyl-L-leucinamide, bis(1,1-dimethylethyl)ester in 6 ml of dimethylformamide was treated with dimethylamine, as described in Example 39, giving 0.2 g of the desired product, mp 255° C. (dec.).

EXAMPLE 138

[S-(R*,R*,R*,R*)]-4,4'-[(9,10-Dihydro-5,8-dihydroxy-9,10-dioxo-1,4-anthracenediyl)bis-imino-2,1-ethanediylimino)]bis[3-[(2-amino-4-methyl-1-oxopentyl)amino]-4-oxobutanoic acid], bis(trifluoroacetate)

A solution of 100 mg of [S-(R*,R*,R*,R*)]-4,4'-(9,10-dihydro-5,8-dihydroxy-9,10-dioxo-1,4-anthracenediyl)-bis(imino-2,1-ethanediylimino)]bis[3-[(2-amino-4-methyl-1-oxopentyl)amino]butanoic acid], bis(1,1-dimethylethyl)ester in 1 ml of anisole was slurried at ice bath temperature and 2 ml of trifluoroacetic acid was added. After 15 minutes at 5° C. and 75 minutes at room temperature the reaction was quenched with an excess of ether, giving mg of the desired product, mp 144° C. (dec.).

EXAMPLE 139

N,N'-[(9,10-Dihydro-5,8-dihydroxy-9,10-dioxo-1,4-anthracenediyl)bis(imino-2,1-ethanediyl)]bis[L-α-aspartyl-L-leucyl-L-alanyl-L-leucinamide], bis(trifluoroacetate)

A 100 mg portion of N,N'-[(9,10-dihydro-5,8-dihydroxy-9,10-dioxo-1,4-anthrancediyl)bis(imino-2,1-ethanediyl)]bis[L-α-aspartyl-L-leucyl-L-alanyl-L-leucinamide], bis(1,1-dimethylethyl)ester was reacted as described in Example 138, giving 67 mg of the desired product, mp 223° C. (dec.).

EXAMPLE 140

N,N'-[(9,10-Dihydro-5,8-dihydroxy-9,10-dioxo-1,4-anthracenediyl)bis[imino-2,1-ethanediylimino[1-carboxymethyl)-2-oxo-2,1-ethanediyl]]]bis[L-leucyl-L-alanyl-L-leucinamide], bis(trifluoroacetate)

Treatment of 36 mg of N,N'-[(9,10-dihydro-5,8-dihydroxy-9,10-dioxo-1,4-anthracenediyl)bis(imino-2,1-ethanediylimino)]bis[[1-[2-(1,1-dimethylethoxy)-2-oxoethyl]-2-oxoethyl]-2-oxo-2,1-ethanediyl]bis[L-leucyl-L-alanyl-L-leucinamide] with 0.35 ml of anisole and 0.7 ml of trifluoroacetic acid, as described in Example 138, gave 31 mg of the desired product, mp 200° C. (dec.).

EXAMPLE 141

N,N'-[(9,10-Dihydro-5,8-dihydroxy-9,10-dioxo-1,4-anthracenediyl)bis(imino-2,1-ethanediyl)]bis[glycylgylycyl-L-α-aspartyl-L-alanyl-L-leucinamide], bis(trifluoroacetate)

Treatment of 50 mg of N,N'-[(9,10-dihydroxy-9,10-dioxo-1,4-anthracenediyl)bis(imino-2,1-ethanediyl)]bis[gycylglycyl-L-α-aspartyl-L-alanyl-L-leucinamide], bis(1,1-dimethylethyl)ester with 0.5 ml of anisole and 1 ml of trifluoroacetic acid, as described in Examle 138, gave 44 mg of the desired product, mp 190° C. (dec.).

EXAMPLE 142

N,N'-[(9,10-Dihydro-5,8-dihydroxy-9,10-dioxo-1,4-anthracenediyl)bis(imino-2,1-ethanediyl)]bis[glycyl-L-α-aspartyl-L-alanyl-L-leucinamide], bis(trifluoroacetate)

Treatment of 32 mg of N,N'-[(9,10-dihydro-5,8-dihydroxy-9,10-dioxo-1,4-anthracenediyl)bis(imino-2,1-ethanediyl)]bis[glycyl-L-α-aspartyl-L-alanyl-L-leucinamide], bis(1,1-dimethylethyl)ester with 0.35 ml of anisole and 0.7 ml of trifluoroacetic acid, as described in Example 138, gave 27 mg of the desired product, mp 200° C. (dec.).

EXAMPLE 143

[S-(R*,R*)]-[(9,10-Dihydro-5,8-dihydroxy-9,10-dioxo-1,4-anthracenediyl)bis[imino-2,1-ethanediyl-[(2-hydroxyethyl)imino](1-methyl-2-oxo-2,1-ethanediyl)]]bis-carbamic acid, bis(1,1-dimethylethyl)ester Following the procedure of Example 2, 1.14 g of t-butoxycarbonyl-L-alanine was reacted with 0.62 g of dicyclohexylcarbodiimide in 25 ml of dimethylformamide to form the symmetrical anhydride. This was then reacted with 0.444 g of 1,4-dihydroxy-5,8-bis[[2-(2-hydroxyethylamino)ethyl]amino]anthraquinone in 40 ml of dimethylformamide overnight. The solvent was evaporated and the residue triturated with ether, giving 0.64 g of the desired product, mp 130° C. (dec.).

EXAMPLE 144

[R-(R*,R*)]-[(9,10-Dihydro-5,8-dihydroxy-9,10-dioxo-1,4-anthracenediyl)bis[imino-2,1-ethanediyl-[(2-hydroxyethyl)imino](1-methyl-2-oxo-2,1-ethanediyl)]]bis-carbamic acid, bis(1,1-dimethylethyl)ester Repeating the procedure of Example 143, using D-alanine in place of L-alanine, gave 0.67 g of the desired product, mp 118° C. (dec.).

EXAMPLE 145

[S-(R*,R*)]-N,N'-[(9,10-Dihydro-5,8-dihydroxy-9,10-dioxo-1,4-anthracenediyl)bis[imino-2,1-ethanediyl)-]bis[2-amino-N-(2-hydroxyethyl)propanamide], bis(trifluoroacetate)

Using the method of Example 27, 0.4 g of [S-(R*,R*)]-[(9,10-dihydro-5,8-dihydroxy-9,10-dioxo-1,4-anthracenediyl)-bis[imino-2,1-ethanediyl[(2-hydroxyethyl)imino](1-methyl-2-oxo-2,1-ethanediyl)]]bis-carbamic acid, bis(1,1-dimethylethyl)ester was reacted with 4 ml of anisole and 8 ml of trifluoroacetic acid, giving 0.36 g of the desired product, mp 145° C. (dec.).

EXAMPLE 146

[R-(R*,R*)]-N,N'-[(9,10-Dihydro-5,8-dihydroxy-9,10-dioxo-1,4-anthracenediyl)bis[imino-2,1-ethanediyl)-]bis[2-amino-N-(2-hydroxyethyl)]propanamide, bis(trifluoroacetic)

Repeating Example 145, but using [R*,(R*,R*)]-[(9,10-dihydro-5,8-dihydroxy-9,10-dioxo-1,4-anthracenediyl)bis[imino-2,1-ethanediyl[(2-hydroxyethyl)imino](1-methyl-2-oxo-2,1-ethanediyl)]]bis-carbamic acid, bis(1,1-dimethylethyl)ester, gave 0.4 g of the desired product, mp 149° C. (dec.).

We claim:

1. A compound selected from the group consisting of those of the formula:

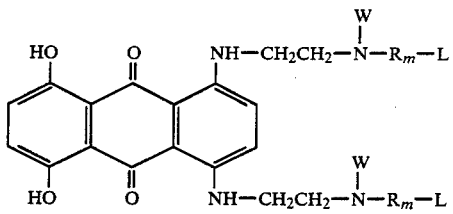

wherein m is an integer from 1 to 10, inclusive; W is hydrogen or β-hydroxyethyl; L is hydrogen, carbobenzyloxy, tert.-butyloxycarbonyl or fluorenylmethoxycarbonyl; and each R group is an amino acid moiety independently selected from the group of D or L amino acids consisting of cysteine, leucine, isoleucine, phenylalanine, typrosine, proline, tryptophan, hydroxyproline, aspartic acid, asparagine, glutamic acid, glutamine, lysine, ornithine, arginine, histidine, alanine, glycine, methionine, valine, threonine and serine which are linked through amide bonds between the α-amino functionality of one amino acid and the carboxyl group of the adjacent amino acid and wherein any side-chain functionality may be substituted by protecting groups thereon; and the pharmacologically acceptable acid-addition salts thereof.

2. The compound according to claim 1; N,N'[(9,10-dihydro-5,8-dihydroxy-9,10-dioxo-1,4-anthracenediyl)-bis(imino-2,1-ethanediyl]bis[2-aminoacetamide], dihydrochloride.

3. The compound according to claim 1; [S-(R*,R*)]-5,5,'-(9,10-dihydro-5,8-dihydroxy-9,10-dioxo-1,4-anthracendeiyl)bis(imino-2,1-ethanediylimino)]bis-[4-amino-5-oxo-pentanoic acid], dihydrochloride.

4. The compound according to claim 1; [2S-(2R*,2'R*,3S*,3'S*)]-N,N'-[(9,10-dihydro-5,8-dihydroxy-9,10-dioxo-1,4-anthracenediyl)bis(imino-2,1-ethanediyl)]bis [2-amino-3-hydroxybutanamide]-bis(trifluoroacetate).

5. The compound according to claim 1; [S-(R*,R*)]-N,N'](9,10-dihydro-5,8-dihydroxy-9,10-dioxo-1,4-anthracenediyl)bis (imino-2,1-ethanediyl)]bis[2,6-diaminohexamide], tetrahydrobromide.

6. The compound according to claim 1; [S-(R*,R*)]-4,4',[(9,10-dihydro-5,8-dihydroxy-9,10-dioxo-1,4-anthracenediyl)bis(imino-2,1-ethancdiylimino)]bis[3-amino-4-oxobutanoic acid[bis(trifluoroacetate).

7. The compound according to claim 1; N,N'[(9,10-dihydro-5,8-dihydroxy-9,10-dioxo-1,4-anthraceneiyl)-bis(imino-2,1-ethanediyl)]bis[L-leucyl-L-alaninamide], dihydrobromide.

8. The compound according to claim 1; N,N'-[(9,10-dihydro-5,8-dihydroxy-9,10-dioxo-1,4-anthracenediyl)-bis(imino-2,1-ethanediyl)]bis[L-alanyl-glycinamine]-dihydrobromide.

9. The compound according to claim 1; N,N'[(9,10-dihydro-5,8-dihydroxy-9,10-dioxo-1,4-anthracenediyl)-bis(imino-2,1-ethanediyl)]bis[N-[(1,1-(-dimethylethoxy)carbonyl]-L-alanyl-L-alanyl-L-leucinamide].

10. The compound according to claim 1; N,N'[(9,10-dihydro-5,8-dihydroxy-9,10-dioxo-1,4-anthracenediyl)-bis(imino-2,1-ethanediyl)]bis-[glycylglycyl-L-leucinamide]dihydrobromide.

11. The compound according to claim 1; N,N'[(9,10-dihydro-5,8-dihydroxy-9,10-dioxo-1,4-anthracenediyl)- bis(imino-2,1-ethanediyl)]bis[L-alanyl-L-alanyl-L-alanine]bis(trifluoroacetate).

12. The compound according to claim 1; N,N'[(9,10-dihydro-5,8-dihydroxy-9,10-dioxo-1,4-anthracenediyl)-bis(imino-2,1-ethanediyl)]bis[-L-alpha-aspartyl-L-alanyl-L-alaninamide]bis-(trifluoroacetate).

13. The compound according to claim 1; N,N'[(9,10-dihydro-5,8-dihydroxy,9,10-dioxo-1,4-anthracenediyl)-bis(imino-2,1-ethanediyl)]bis-[L-alanyl-L-argininamide[tetrahydrobromide.

14. The compound according to claim 1; N,N'[(9,10-dihydro-5,8-dihydroxy,9,10-dioxo-1,4-anthracenediyl)-bis(imino-2,1-ethanediyl)]bis-[glycylglycyl-L-alpha-aspartyl-L-alaninamide].

15. The compound according to claim 1; N,N'-[(9,10-dihydro-5,8-dihydroxy-9,10-dioxo-1,4-anthracenediyl)-bis(imino-2,1-ethanediyl)]bis-[L-alpha-aspartyl-L-alaninamide], bis(trifluoroacetate).

16. The compound according to claim 1; [S-(R*,R*)]-N,N'-[(9,10-dihydro-5,8-dihydroxy-9,10-dioxo-1,4-anthracenediyl)bis(imino-2,1-ethanediyl)]bis[2,6-diamino-N-(2-hydroxyethyl)-hexanamide]tetrakis(trifluoroacetate).

17. The compound according to claim 1; N,N'-[(9,10-dihydro-5,8-dihydroxy-9,10-dioxo-1,4-anthracenediyl)-bis[imino-2,1-ethanediylamino[(1-carboxymethyl)-2-oxo-2,1-ethanediyl]]]bis[L-leucyl-L-alanyl-L-leucinamide], is (trifluoroacetate).

18. The compound according to claim 1; N,N'-[(9,10-dihydro-5,8-dihydroxy-9,10-dioxo-1,4-anthracenediyl)-bis(imino-2,1-ethanediyl)]bis-[glycylglycyl-L-alpha-aspartyl-L-alanyl-L-leucinamide], bis(trifluoroacetate).

19. The compound according to claim 1; [S-(R*,R*)]-N,N'-[(9,10-dihydro-5,8-dihydroxy-9,10-dioxo-1,4-anthracenediyl)bis]imino-2,1-ethanediyl)]]-bis[2-amino-N-(2-hydroxyethyl)propanamide], bis(trifluoroacetate).

20. The compound according to claim 1; N,N'-[(9,10-dihydro-5,8-dihydroxy-9,10-dioxo-1,4-anthracenediyl)-bis(imino-2,1-ethanediyl)]bis-[L-alpha-aspartyl-L-seryl-L-alanyl-L-leucyl-L-leucinamide]bis(trifluoroacetate).

* * * * *